US008828960B2

(12) United States Patent
Murthy et al.

(10) Patent No.: US 8,828,960 B2
(45) Date of Patent: Sep. 9, 2014

(54) AMINO ACID VITAMIN ESTER COMPOSITIONS FOR CONTROLLED DELIVERY OF PHARMACEUTICALLY ACTIVE COMPOUNDS

(75) Inventors: Yerramilli V.S.N. Murthy, Apex, NC (US); Michael Atkinson, Cary, NC (US)

(73) Assignee: IDEXX Laboratories, Inc., Westbrook, ME (US)

( * ) Notice: Subject to any disclaimer, the term of this patent is extended or adjusted under 35 U.S.C. 154(b) by 1186 days.

(21) Appl. No.: 12/171,353

(22) Filed: Jul. 11, 2008

(65) Prior Publication Data

US 2009/0023678 A1 Jan. 22, 2009

Related U.S. Application Data

(60) Provisional application No. 60/929,903, filed on Jul. 17, 2007, provisional application No. 60/960,891, filed on Oct. 18, 2007.

(51) Int. Cl.
*A61K 31/7088* (2006.01)
*A61K 31/223* (2006.01)
*A61K 31/67* (2006.01)
*A61K 45/06* (2006.01)
*A61K 31/198* (2006.01)
*A61K 31/59* (2006.01)
*A61K 8/67* (2006.01)

(52) U.S. Cl.
CPC ............... *A61K 45/06* (2013.01); *A61K 31/223* (2013.01); *A61K 31/198* (2013.01); *A61K 31/7088* (2013.01); *A61K 31/59* (2013.01); *A61K 8/67* (2013.01)
USPC ........ 514/44 R; 514/44 A; 514/458; 514/474; 514/784; 514/785

(58) Field of Classification Search
CPC ......... A61K 8/67; A61K 8/671; A61K 8/673; A61K 8/676; A61K 8/678; A61K 31/713; A61K 31/198; A61K 31/223
See application file for complete search history.

(56) References Cited

U.S. PATENT DOCUMENTS

| 5,270,163 | A | 12/1993 | Gold et al. | |
|---|---|---|---|---|
| 5,332,834 | A | 7/1994 | Bhattacharya et al. | |
| 5,459,127 | A | 10/1995 | Felgner et al. | |
| 5,475,096 | A | 12/1995 | Gold et al. | |
| 5,574,020 | A | 11/1996 | Klink et al. | |
| 5,599,969 | A | 2/1997 | Hardy et al. | |
| 5,629,020 | A | 5/1997 | Leone-Bay et al. | |
| 5,788,983 | A | 8/1998 | Chien et al. | |
| 5,877,212 | A | 3/1999 | Yu et al. | |
| 6,096,813 | A | 8/2000 | Schimmel et al. | |
| 6,864,284 | B2 * | 3/2005 | Roomi et al. | 514/474 |
| 6,887,487 | B2 | 5/2005 | Murthy et al. | |
| 6,946,137 | B2 | 9/2005 | Murthy et al. | |
| 7,038,026 | B2 | 5/2006 | Crouzet et al. | |
| 7,056,704 | B2 | 6/2006 | Tuschl et al. | |
| 7,078,196 | B2 | 7/2006 | Tuschl et al. | |
| 2003/0165434 | A1 | 9/2003 | Reinhard et al. | |
| 2004/0191763 | A1 | 9/2004 | Delaney et al. | |
| 2004/0197408 | A1 | 10/2004 | Gravett | |
| 2004/0220264 | A1 | 11/2004 | Yu et al. | |
| 2005/0124565 | A1 | 6/2005 | Diener et al. | |
| 2005/0175708 | A1 | 8/2005 | Carrasquillo et al. | |
| 2005/0192348 | A1 | 9/2005 | Bar-Or et al. | |
| 2006/0122144 | A1 | 6/2006 | Kane et al. | |
| 2006/0167088 | A1 | 7/2006 | Widder et al. | |
| 2007/0111969 | A1 | 5/2007 | Murthy | |

FOREIGN PATENT DOCUMENTS

| DE | 43 44 751 | 6/1995 |
|---|---|---|
| WO | WO 99/24417 | 5/1999 |
| WO | WO 03/034988 | 5/2003 |
| WO | WO03/034988 | 5/2003 |
| WO | WO2004089239 | 10/2004 |
| WO | WO2005000241 | 1/2005 |
| WO | WO 2006/050002 | 5/2006 |

OTHER PUBLICATIONS

Search Report for PCT/US05/34415 dated Apr. 4, 2006.
Search Report and Written Opinion corresponding to the PCT/US 08/69951 application dated Dec. 4, 2008.
Matsushima et al: "Molecular species of schiff bases derived from 0-hydroxyaromatic aldehydes. III. Schiff bases of pyridoxal and its analogs with unsaturated amino acids" Chemical and Pharmaceutical Bulletin, Pharmaceutical Society of Japan, Tokyo, vol. 27, No. 3, Jan. 1, 1979, pp. 703-709.
Takata et al: "Vitamin K prodrugs: 1. Synthesis of amino acid esters of menahydroquinone-4 and enzymatic reconversion to an active form" Pharmaceutical Research, Kluwer Academic Publishers, New York, NY, US, vol. 12, No. 1, Jan. 1, 1995, pp. 18-23.
Supplementary European Search Report of EP08796181 application, (2010).
S. M. Elbashir, et al. Genes Dev. 15 (2001) 188-200.
Nagesh Mahanthappa, Pharmacogenomics, 6(8):879-83 Dec. 2005.
D. Baumerof et al., Nature Chemical Biology, 2(12):711-9 Dec. 2006.
Karkare et al., Appl. Biochem BioTechnol. 119(1):1-12 Oct. 2004.
Griffin, et al. (1993) Gene, 137(1):25-31.

(Continued)

*Primary Examiner* — Bong-Sook Baek
(74) *Attorney, Agent, or Firm* — Haynes and Boone, LLP

(57) ABSTRACT

The invention relates to pharmaceutical compositions that provide sustained-release of a pharmaceutically active compound and to methods of treating or preventing a condition in an animal by administering the pharmaceutical compositions to the animal. When the pharmaceutical compositions are administered to an animal by injection, they form a drug depot that releases the pharmaceutically active compound over time. The pharmaceutical compositions can also be administered orally.

19 Claims, No Drawings

(56) References Cited

OTHER PUBLICATIONS

Jenison, et al. (1998) Antisense Nucleic Acid Drug Dev., 8(4):265-79.
Bell, et al. (1999) In Vitro Cell. Dev. Biol. Anim.35(9):533-42.
Watson, et al. (2000) Antisense Nucleic Acid Drug Dev., 10(2):63-75.
Daniels, et al. (2002) Anal. Biochem, 305(2):214-26.
Chen, et al. (2003) Proc. Natl. Acad. Sci. U.S.A. 100(16):9226-31.
Khati, et al. (2003) J. Virol., 77(23): 12692-8.
Vaish, et al. (2003) Biochemistry 42(29):8842-51.
Ellington and Szostak (1990) Nature, 346 (6287):818-22.
Tuerk and Gold (1990), Science, 249 (4968):505-510.
Wlotzka, et al. (2002) Proc. Natl. Acad. Sci. U.S.A., 99(13):8898-902.
Reyderman and Stavchansky (1998), Pharmaceutical Research, 15 (6): 904-10.
Tucker et al. (1999) J. Chromatography B., 732: 203-212.
Watson, et al., (2000) Antisense Nucleic Acid Drug Dev., 10 (2): 63-75.
Green, et al. (1995) Chem. Biol. 2(10): 638-95.
Jellinek, et al. (1995) Biochemistry, 34(36):11363-72.
Ruckman, et al. (1998) J. Biol. Chem., 273 (32):20556-67.
Uhlmann, et al. (2000) Methods Enzymol., 313: 268-84.
P. Burmeister, et al. (2004) Chemistry and Biology: 15, 25-33.

* cited by examiner

AMINO ACID VITAMIN ESTER COMPOSITIONS FOR CONTROLLED DELIVERY OF PHARMACEUTICALLY ACTIVE COMPOUNDS

CROSS REFERENCE TO RELATED APPLICATIONS

This application claims the benefit of U.S. Provisional Application Ser. Nos. 60/929,903 and 60/960,891, filed Jul. 17, 2007 and Oct. 18, 2007, respectively, the contents of which are expressly incorporated herein.

1. STATEMENT REGARDING FEDERALLY SPONSORED RESEARCH OR DEVELOPMENT

Not Applicable.

2. INCORPORATION BY REFERENCE OF MATERIAL SUBMITTED ON A COMPACT DISC

Not Applicable.

3. FIELD OF THE INVENTION

The invention relates to sustained-release pharmaceutical compositions and to methods of administering pharmaceutically active compounds to an animal using the sustained-release pharmaceutical compositions.

4. BACKGROUND OF THE INVENTION

It is often desirable to administer drugs using controlled- or sustained-release formulations that can maintain therapeutic blood levels of the drug over extended periods of time. These controlled release formulations reduce the frequency of dosing, for enhanced convenience and compliance, and also reduce the severity and frequency of side effects. By maintaining substantially constant blood levels and avoiding blood level fluctuations of the drug, such as are associated with conventional immediate release formulations that are administered several times a day, controlled- or sustained-release formulations can provide a better therapeutic profile than is obtainable with conventional immediate release formulations.

Known methods for controlled- or sustained-drug release include implanted devices, such as osmotic pumps, and drug dispersed in a biocompatible polymer matrix, which can be implanted, administered orally, or injected. Examples of biocompatible polymers used in such applications include poly(lactic acid) and poly(lactic acid-co-glycolic acid). The polymer typically undergoes slow hydrolysis in vivo to continually release the entrapped drug over time. The polymer degradation products are non-toxic and absorbed or metabolized by the body. For example, when the biocompatible polymer is poly(lactic acid) or poly(lactic acid-co-glycolic acid), the degradation products are the parent acids, lactic acid and glycolic acid, which are absorbed by the body.

International published application WO 03/034988 discloses compositions of a salt of a pharmacologically active compound and a lipophilic counterion and a pharmaceutically acceptable water soluble solvent that are combined together to provide an injectable composition. When injected into an animal at least a part of the composition precipitates to form a depot that slowly releases the pharmacologically active compound over time.

U.S. patent application no. US 2004/0220264 discloses compositions, methods of making the compositions, and uses of compositions that include a molecular complex between an acidic pharmaceutical drug and a functional substance. The functional substance can be an alkaline amino acid, an amino acid amide, an amino acid ester, or a related amino acid. The compositions are allegedly useful for delivering the drug into cutaneous tissue.

U.S. patent application no. US 2004/0197408 discloses formulations of a diblock copolymer having a hydrophobic block and hydrophilic block, an additive selected from an amino acid, and an oligopeptide. The formulations, when admixed with water, form drug delivery vehicles in micellar form.

Oligonucleotides are small double-stranded or single-stranded segments of DNA or RNA, typically about 20-30 nucleotide bases in length. Oligonucleotides can be synthetic or natural, and bind to a particular target molecule, such as a protein, metabolite, or other nucleic acid sequence. Oligonucleotides are a promising class of therapeutic agents currently in pre-clinical and clinical development for treating a variety of diseases and disorders. Like biologics, e.g., peptides or monoclonal antibodies, oligonucleotides are capable of binding specifically to molecular targets and, through binding, inhibiting target function. Oligonucleotides include for example, siRNA and aptamers.

SiRNA are small strands of RNA that interfere with the translation of messenger RNA. SiRNA can be double stranded or single stranded. Generally, double stranded siRNA works better than single stranded siRNA. Typically, siRNA are about 20 to 25 nucleotides long. SiRNA can be used to interfere with the expression of genes. They bind to the complementary portion of the target messenger RNA and tag it for degradation. SiRNA's effect of inhibiting gene expression is commonly known as gene "silencing." The siRNA causes the destruction of messenger RNA that shares sequence homology with the siRNA to within one nucleotide resolution (Elbashir S. M. et al, *Genes Dev.*, 15 (2001) 188-200). It is believed that the siRNA and the targeted mRNA bind to an "RNA-induced silencing complex" or "RISC," which cleaves the targeted mRNA. The siRNA is apparently recycled much like a multiple-turnover enzyme, with 1 siRNA molecule capable of inducing cleavage of approximately 1000 mRNA molecules. The siRNA mediated degradation of a mRNA is therefore more effective than currently available technologies for inhibiting expression of a target gene.

The ability to specifically inhibit expression of a target gene by siRNA has obvious benefits. For example, many diseases arise from the abnormal expression of a particular gene or group of genes. SiRNA can be used to inhibit the expression of the deleterious gene and therefore alleviate symptoms of a disease or even provide a cure. For example, genes contributing to a cancerous state or to viral replication could be inhibited. In addition, mutant genes causing dominant genetic diseases such as myotonic dystrophy could be inhibited. Inflammatory diseases such as arthritis could also be treated by inhibiting such genes as cyclooxygenase or cytokines. Examples of targeted organs include, but are not limited to the liver, pancreas, spleen, skin, brain, prostrate, heart. In addition, siRNA could be used to generate animals that mimic true genetic "knockout" animals to study gene function. Useful sequences of siRNA can be identified using known procedures such as described in *Pharmacogenomics*, 6(8):879-83 (December 2005), *Nat. Chem. Biol.*, 2(12):711-9

(December 2006), *Appl Biochem. Biotechnol.*, 119(1): 1-12 (October 2004), U.S. Pat. No. 7,056,704 and U.S. Pat. No. 7,078,196).

Aptamers, are oligonucleotides that bind to a particular target molecule, such as a protein or metabolite. Typically, the binding is through interactions other than classic Watson-Crick base pairing. A typical aptamer is 10-15 kDa in size (i.e., 30-45 nucleotides), binds its target with sub-nanomolar affinity, and discriminates among closely related targets (e.g., will typically not bind other proteins from the same gene family) (Griffin, et al. (1993), *Gene*, 137(1): 25-31; Jenison, et al. (1998), *Antisense Nucleic Acid Drug Dev.*, 8(4): 265-79; Bell, et al. (1999), *In Vitro Cell. Dev. Biol. Anim.*, 35(9): 533-42; Watson, et al. (2000), *Antisense Nucleic Acid Drug Dev.*, 10(2): 63-75; Daniels, et al. (2002), *Anal. Biochem.*, 305(2): 214-26; Chen, et al. (2003), *Proc. Natl. Acad. Sci. U.S.A.*, 100(16): 9226-31; Khati, et al. (2003), *J. Virol.*, 77(23): 12692-8; Vaish, et al. (2003), *Biochemistry*, 42(29): 8842-51).

Aptamers can be created by an entirely in vitro selection process (Systematic Evaluation of Ligands by Experimental Enrichment, i.e., SELEX™) from libraries of random sequence oligonucleotides as described in U.S. Pat. Nos. 5,475,096 and 5,270,163. Aptamers have been generated against numerous proteins of therapeutic interest, including growth factors, enzymes, immunoglobulins, and receptors (Ellington and Szostak (1990), *Nature*, 346(6287): 818-22; Tuerk and Gold (1990), *Science*, 249(4968): 505-510).

Aptamers have a number of attractive characteristics for use as therapeutics. In addition to high target affinity and specificity, aptamers have shown little or no toxicity or immunogenicity in standard assays (Wlotzka, et al. (2002), *Proc. Natl. Acad. Sci. U.S.A.*, 99(13): 8898-902). Indeed, several therapeutic aptamers have been optimized and advanced through varying stages of pre-clinical development, including pharmacokinetic analysis, characterization of biological efficacy in cellular and animal disease models, and preliminary safety pharmacology assessment (Reyderman and Stavchansky (1998), *Pharmaceutical Research*, 15(6): 904-10; Tucker et al., (1999), *J. Chromatography B.*, 732: 203-212; Watson, et al. (2000), *Antisense Nucleic Acid Drug Dev.*, 10(2): 63-75).

Oligonucleotides, to be effective, must be distributed to target organs and tissues, and remain in the body (unmodified) for a period of time consistent with the desired dosing regimen. In addition, siRNA, to be effective, must enter the cell. Aptamers, however, are directed against extracellular targets and, therefore, do not suffer from difficulties associated with intracellular delivery.

It is important, however, that the pharmacokinetic properties for all oligonucleotide-based therapeutics be tailored to match the desired pharmaceutical application. Early work on nucleic acid-based therapeutics has shown that, while unmodified oligonucleotides are degraded rapidly by nuclease digestion, protective modifications at the 2'-position of the sugar, and use of inverted terminal cap structures, e.g., [3'-3'dT], dramatically improve nucleic acid stability in vitro and in vivo (Green, et al. (1995), *Chem. Biol.*, 2(10): 683-95; Jellinek, et al. (1995), *Biochemistry*, 34(36): 11363-72; Ruckman, et al. (1998), *J. Biol. Chem.*, 273(32): 20556-67; Uhlmann, et al. (2000), *Methods Enzymol.*, 313: 268-84). For example, in some SELEX selections (i.e., SELEX experiments or SELEX ions), the starting pools of nucleic acids from which aptamers are selected are typically pre-stabilized by chemical modification, for example by incorporation of 2'-fluoropyrimidine (2'-F) substituted nucleotides, to enhance resistance of the aptamers against nuclease attack. Aptamers incorporating 2'-O-methylpurine (2'-OMe purine) substituted nucleotides have also been developed through post-SELEX modification steps or, more recently, by enabling synthesis of 2'-OMe-containing random sequence libraries as an integral component of the SELEX process itself.

In addition to clearance by nucleases, oligonucleotide therapeutics are subject to elimination via renal filtration. As such, a nuclease-resistant oligonucleotide administered intravenously exhibits an in vivo half-life of <10 min, unless filtration can be blocked. This can be accomplished by either facilitating rapid distribution out of the blood stream into tissues or by increasing the apparent molecular weight of the oligonucleotide above the effective size cut-off for the glomerulus. Conjugation to a PEG polymer ("PEGylation") can dramatically lengthen residence times of oligonucleotides in circulation, thereby decreasing dosing frequency and enhancing effectiveness against targets. Previous work in animals has examined the plasma pharmacokinetic properties of PEG-conjugated aptamers (Reyderman and Stavchansky (1998), *Pharmaceutical Research*, 15(6): 904-10; Watson, et al. (2000), *Antisense Nucleic Acid Drug Dev.*, 10(2): 63-75)). Determining the extravasation of an oligonucleotide therapeutic, including oligonucleotide therapeutics conjugated to a modifying moiety or containing modified nucleotides and, in particular, determining the potential of oligonucleotides or their modified forms to access diseased tissues (for example, sites of inflammation, or the interior of tumors) define the spectrum of therapeutic opportunities for oligonucleotide intervention.

Typically, therapeutic oligonucleotides are administered by injection, for example, by subcutaneous or intravenous injection. Accordingly, the oligonucleotides must be dissolved or dispersed in a liquid vehicle for administration. The relatively high molecular weight of oligonucleotides, and in particular oligonucleotides that have been derivatized, for example by PEGylation, however, often makes it difficult to obtain a pharmaceutical composition wherein the oligonucleotide is dissolved or dispersed in a pharmaceutically acceptable solvent at a sufficient concentration to provide a pharmaceutical composition that is clinically useful for administration to an animal.

U.S. published application no. 2005/0175708 discloses a composition of matter that permits the sustained delivery of aptamers to a mammal. The aptamers are administered as microspheres that permit sustained release of the aptamers to the site of interest so that the aptamers can exert their biological activity over a prolonged period of time. The aptamers, can be anti-VEGF aptamers.

P. Burmeister et al., (2004), *Chemistry and Biology*: 15, 25-33 disclose a method for generating a 2'-O-methyl aptamer (ARC245) that binds to vascular endothelial growth factor, which exhibits good stability.

There remains a need in the art, however, for therapeutic agent containing pharmaceutical compositions, suitable for injection or implantation, wherein the formulation provides controlled- or sustained-release of the therapeutic agent. There is also a need in the art for improved pharmaceutical compositions, wherein the therapeutic agent is an oligonucleotide. In particular, there is a need for pharmaceutical composition wherein the oligonucleotide can be dissolved or dispersed in a pharmaceutically acceptable solvent at a sufficient concentration to provide a pharmaceutical composition that is clinically useful for administration to an animal, and, in particular, administration by injection. The present invention addresses this as well as other needs.

Citation of any reference in Section 4 of this application is not to be construed that such reference is prior art to the present application.

5. SUMMARY OF THE INVENTION

The invention relates to a pharmaceutical composition comprising:
(i) an amino acid-vitamin ester,
(ii) an acidic pharmaceutically active compound, and
(iii) a pharmaceutically acceptable organic solvent,
wherein the pharmaceutical composition is injectable and forms a precipitate when injected into water.

The invention further relates to a pharmaceutical composition comprising:
(i) an amino acid-vitamin ester,
(ii) a carboxylic acid,
(iii) a pharmaceutically active compound selected from the group consisting of a neutral non-acidic pharmaceutically active compound and a pharmaceutically acceptable salt of a pharmaceutically active compound, and
(iv) a pharmaceutically acceptable organic solvent,
wherein the pharmaceutical composition is injectable and forms a precipitate when injected into water.

The invention further relates to a pharmaceutical composition comprising:
(i) a protonated oligonucleotide,
(ii) an amino acid-vitamin ester, and
(iii) a pharmaceutically acceptable organic solvent,
wherein the pharmaceutical composition is injectable and forms a precipitate when injected into water.

The invention further relates to methods of treating a condition in an animal comprising administering to an animal in need thereof a pharmaceutical composition of the invention.

6. DETAILED DESCRIPTION OF THE INVENTION

The invention relates to pharmaceutical compositions for administering pharmaceutically active compounds. The compositions provide sustained- or controlled-release of the pharmaceutically active compound. The invention further relates to methods of treating a condition in an animal comprising administering to an animal in need thereof a pharmaceutical composition of the invention.

The invention relates to a pharmaceutical composition comprising:
(i) an amino acid-vitamin ester and
(ii) an acidic pharmaceutically active compound.

In one embodiment, the pharmaceutical composition is a solid.

In one embodiment, the pharmaceutical composition further comprises a pharmaceutically acceptable organic solvent. Accordingly, the invention further relates to a pharmaceutical composition comprising:
(i) an amino acid-vitamin ester,
(ii) an acidic pharmaceutically active compound, and
(iii) a pharmaceutically acceptable organic solvent.

In one embodiment, the pharmaceutical composition further comprising a pharmaceutically acceptable organic solvent comprises a suspension of solid particles in the pharmaceutically acceptable organic solvent. In one embodiment, the pharmaceutical composition further comprising a pharmaceutically acceptable organic solvent is injectable. In one embodiment, the pharmaceutical composition further comprising a pharmaceutically acceptable organic solvent is a solution. In one embodiment, the pharmaceutical composition further comprising a pharmaceutically acceptable organic solvent is injectable and forms a precipitate when injected into water.

The invention further relates to a pharmaceutical composition comprising:
(i) an amino acid-vitamin ester,
(ii) a carboxylic acid, and
(iii) a pharmaceutically active compound selected from the group consisting of a neutral non-acidic pharmaceutically active compound and a pharmaceutically acceptable salt of a pharmaceutically active compound.

In one embodiment, the pharmaceutical composition is a solid.

In one embodiment, the pharmaceutical composition further comprises a pharmaceutically acceptable organic solvent. Accordingly, the invention further relates to a pharmaceutical composition comprising:
(i) an amino acid-vitamin ester,
(ii) a carboxylic acid,
(iii) a pharmaceutically active compound selected from the group consisting of a neutral non-acidic pharmaceutically active compound and a pharmaceutically acceptable salt of a pharmaceutically active compound, and
(iv) a pharmaceutically acceptable organic solvent.

In one embodiment, the pharmaceutical composition further comprising a pharmaceutically acceptable organic solvent comprises a suspension of solid particles in the pharmaceutically acceptable organic solvent. In one embodiment, the pharmaceutical composition further comprising a pharmaceutically acceptable organic solvent is injectable. In one embodiment, the pharmaceutical composition further comprising a pharmaceutically acceptable organic solvent is a solution. In one embodiment, the pharmaceutical composition further comprising a pharmaceutically acceptable organic solvent is injectable and forms a precipitate when injected into water.

The invention further relates to a pharmaceutical composition comprising:
(i) a protonated oligonucleotide, and
(ii) an amino acid-vitamin ester.

In one embodiment, the pharmaceutical composition is a solid.

In one embodiment, the pharmaceutical composition further comprises a pharmaceutically acceptable solvent. Accordingly, the invention further relates to a pharmaceutical composition comprising:
(i) a protonated oligonucleotide,
(ii) an amino acid-vitamin ester, and
(iii) a pharmaceutically acceptable organic solvent.

In one embodiment, the pharmaceutical composition further comprising a pharmaceutically acceptable organic solvent comprises a suspension of solid particles in the pharmaceutically acceptable organic solvent. In one embodiment, the pharmaceutical composition further comprising a pharmaceutically acceptable organic solvent is injectable. In one embodiment, the pharmaceutical composition further comprising a pharmaceutically acceptable organic solvent is a solution. In one embodiment, the pharmaceutical composition further comprising a pharmaceutically acceptable organic solvent is injectable and forms a precipitate when injected into water.

6.1 Definitions

As used herein, the following terms have the following meaning:

The phrase "$C_1$-$C_{22}$ hydrocarbon group" means a straight or branched, saturated or unsaturated, cyclic or non-cyclic, aromatic or non-aromatic, carbocyclic or heterocyclic group having from 1 to 22 carbon atoms. Similarly, "$C_1$-$C_2$, hydrocarbon group," "$C_1$-$C_{18}$ hydrocarbon group," "$C_6$-$C_{18}$ hydrocarbon group," "$C_8$-$C_{18}$ hydrocarbon group," and a "$C_{10}$-$C_{18}$ hydrocarbon group" means a straight or branched, saturated or unsaturated, cyclic or non-cyclic, aromatic or non-aromatic, carbocyclic or heterocyclic group having from 1 to 21 carbon atoms, from 1 to 18 carbon atoms, from 6 to 18 carbon atoms, from 8 to 18 carbon atoms, and from 10 to 18 carbon atoms, respectively. Similar phrases construed in the same way. Accordingly, the phrase "an acyl group of formula —C(O)—$R_5$, wherein $R_5$ is a $C_1$ to $C_{21}$ hydrocarbon group means an acyl group of formula —C(O)—$R_5$, wherein $R_5$ is a straight or branched, saturated or unsaturated, cyclic or non-cyclic, aromatic or non-aromatic, carbocyclic or heterocyclic group having from 1 to 21 carbon atoms. Representative acyl groups of formula —C(O)—$R_5$, wherein $R_5$ is an unsubstituted $C_1$ to $C_{21}$ group include, but are not limited to, acetyl, propionyl, butanoyl, hexanoyl, caproyl, laurolyl, myristoyl, palmitoyl, stearoyl, palmioleoyl, oleoyl, linoleoyl, linolenoyl, and benzoyl.

The term "salt," as used herein, means two compounds that are not covalently bound but are chemically bound by ionic interactions.

The term "pharmaceutically acceptable organic solvent," as used herein, means an organic solvent that when administered to an animal does not have undue adverse effects such as excessive toxicity, irritation, or allergic response commensurate with a reasonable benefit/risk ratio. Preferably, the pharmaceutically acceptable organic solvent is a solvent that is generally recognized as safe ("GRAS") by the United States Food and Drug Administration ("FDA").

The term "water miscible organic solvent," as used herein, means an organic solvent that is capable of mixing with water in any ratio without separating into two phases.

The term "water soluble organic solvent," as used herein, means an organic solvent that has a significant level of solubility in water. In one embodiment, the water soluble organic solvent is soluble in water in an amount of at least about 5 percent by weight. In one embodiment, the water soluble organic solvent is soluble in water in an amount of at least about 10 percent by weight. In one embodiment, the water soluble organic solvent is soluble in water in an amount of at least about 20 percent by weight. In one embodiment, the water soluble organic solvent is soluble in water in an amount of at least about 50 percent by weight. For example, triacetin is considered a water soluble solvent since it is soluble in water at a ratio of about 1:14.

The phrase "forms a precipitate," as used herein, means that the pharmaceutical composition forms a precipitate, or solid, when injected into water or into a physiological (in vivo) environment. A precipitate is an insoluble solid formed in solution at room temperature in vitro or in a physiological (in vivo) environment. The precipitate can take many forms such as, for example, a solid, a crystal, a gummy mass, or a gel. Preferably, the precipitate is a gummy mass or a gel. A composition of the invention forms a precipitate in water when at least 10% of the composition is retained on a 0.22 µm filter when the composition is mixed with water and filtered at 98° F. Typically, to form the precipitate, about 1 mL of the pharmaceutical composition is injected into about 5 mL of water.

The term "fatty acid," as used herein means a carboxylic acid of formula R—C(O)OH, wherein Ra is $C_6$-$C_{22}$ linear or branched, saturated or unsaturated, hydrocarbon group. Representative fatty acids include, but are not limited to, caproic acid, lauric acid, myristic acid, palmitic acid, stearic acid, palmic acid, oleic acid, linoleic acid, and linolenic acid.

The term "fluoroquinolone," as used herein, means any compound having the basic structure:

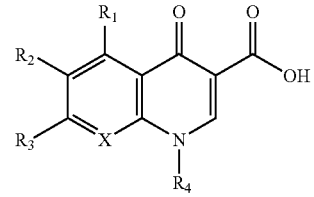

wherein $R_1$, $R_2$, $R_3$, and $R_4$ can be a variety of functional groups and X can be carbon, which may be substituted or unsubstituted, or nitrogen. One skilled in the art would readily recognize fluoroquinolones useful in the compositions and methods of the invention. Typically, the fluoroquinolones are useful as antibiotics but they may also be used to treat other conditions (for example, nephrotic syndromes).

The phrase "injectable" or "injectable composition," as used herein, means a composition that can be drawn into a syringe and injected subcutaneously, intraperitoneally, or intramuscularly into an animal without causing adverse effects due to the presence of solid material in the composition. Solid materials include, but are not limited to, crystals, gummy masses, and gels. Typically, a formulation or composition is considered to be injectable when no more than 10% is retained on a 0.22 µm filter when the formulation is filtered through the filter at 98° F. In one embodiment, no more than 5% of the formulation or composition is retained on a 0.22 µm filter when the formulation is filtered through the filter at 98° F. In one embodiment, no more than 2% of the formulation or composition is retained on a 0.22 µm filter when the formulation is filtered through the filter at 98° F. In one embodiment, no more than 1% of the formulation or composition is retained on a 0.22 µm filter when the formulation is filtered through the filter at 98° F.

The term "solution," as used herein, means a uniformly dispersed mixture at the molecular or ionic level of one or more substances (solute), in one or more other substances (solvent), typically a liquid.

The term "suspension" or "dispersion," as used herein, means solid particles that are evenly dispersed in a solvent, which can be aqueous or non-aqueous. In one embodiment, the particles have an average particle size of less than about 100 µm determined using a particle size analyzer such as commercially available from Microtrac Inc. of Montgomeryville, Pa. or Malvern Instruments of Worcestershire, England. Suspensions can be distinguished from solutions using methods well known to those skilled in the art, for example, using a particle size analyzer.

The term "animal," as used herein, includes, but is not limited to, humans, canines, felines, equines, bovines, ovines, porcines, amphibians, reptiles, and avians. Representative animals include, but are not limited to a cow, a horse, a sheep, a pig, an ungulate, a chimpanzee, a monkey, a baboon, a chicken, a turkey, a mouse, a rabbit, a rat, a guinea pig, a dog, a cat, and a human. In one embodiment, the animal is a mammal. In one embodiment, the animal is a human. In one embodiment, the animal is a canine, a feline, an equine, a bovine, an ovine, or a porcine.

The term "pharmaceutically active compound," as used herein, means a compound that causes a pharmacological effect in an animal. Typically, the pharmacological effect is treating or preventing a condition in an animal.

The term "condition," as used herein means an interruption, cessation, or disorder of a bodily function, system, or organ. Representative conditions include, but are not limited to, infections such as bacterial, viral, fungal and, parasitic infections; diseases such as cancer; inflammation; diabetes; and organ failure.

The term "effective amount," as used herein, means an amount sufficient to treat or prevent a condition in an animal.

The phrase "treating," "treatment of," and the like includes the amelioration or cessation of a specified condition.

The phrase "preventing," "prevention of," and the like include the avoidance of the onset of a condition.

The phrase "drug depot," as used herein means a precipitate that includes the pharmaceutically active compound formed within the body of a treated animal that releases a pharmaceutically effective amount of the pharmaceutically active compound over time.

The phrase "acidic pharmaceutically active compound," as used herein means a pharmaceutically active compound that has an acidic functional group, i.e., a group that is capable of donating a proton to a basic functional group such as an amine group. Representative acidic functional group include, but are not limited to —COOH (i.e., carboxylic acid groups), —S(O)$_2$—OH (i.e., sulfonic acid groups), —OP(O)(OR)(OH), —O(P)(OH)$_2$, —P(O)(OR)(OH), —(P)(OH)$_2$), —OP(O)(R)(OH), and —P(O)(R)(OH), wherein R is a hydrocarbon group that can optionally be substituted.

The phrase "neutral non-acidic pharmaceutically active compound," as used herein means a pharmaceutically active compound that has no net charge and no acidic functional groups. Neutral non-acidic pharmaceutically active compounds include zwitterions.

The phrase "pharmaceutically acceptable salt," as used herein, is a salt formed between an acid and a basic group of a pharmaceutically active compounds. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also refers to a salt formed between a pharmaceutically active compound having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl, N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N,-dimethyl-N-(2-hydroxyethyl)amine, or tri-(2-hydroxyethyl)amine; N-methyl-D-glucamine; and amino acids such as arginine, lysine, and the like.

The phrase "substantially free of," as used herein, means less than about 2 percent by weight, preferably less than about 1 percent by weight, more preferably less than about 0.5 percent by weight, and most preferably less than about 0.2 percent by weight. For example, the phrase "a pharmaceutical composition substantially free of water" means that the amount of water in the pharmaceutical composition is less than about 2 percent by weight of the pharmaceutical composition, preferably less than about 1 percent by weight of the pharmaceutical composition, more preferably less than about 0.5 percent by weight of the pharmaceutical composition, and most preferably less than about 0.2 percent by weight of the pharmaceutical composition.

The term "vitamin," as used herein, is its art recognized meaning, i.e., nutrients required in tiny amounts for essential metabolic reactions in the body. The term vitamin, however, does not include other essential nutrients such as dietary minerals, essential fatty acids, or essential amino acids, nor does it encompass the large number of other nutrients that promote health but that are not essential for life.

The phrase "residue of a vitamin," as used herein, means a vitamin that has a hydroxyl (i.e., —OH group) wherein the hydrogen of the hydroxyl group is removed. For example, if the formula of the vitamin is H—O—R$_1$, the formula for the "residue of the vitamin" will be —OR$_1$.

The term "propylene glycol," as used herein, means CH$_2$(OH)CH$_2$CH$_2$(OH) or CH$_2$(OH)CH$_2$(OH)CH$_3$, i.e., 1,3-propylene glycol or 1,2-propylene glycol.

The term "glycerol formal," as used herein, means an organic solvent of formula C$_4$H$_8$O$_3$ that exists as a mixture of 5-hydroxy-1,3-dioxane and 4-hydroxymethyl-1,3-dioxolane in a ratio of about 60:40. Although the solvent glycerol formal consists of two chemical compounds, the two chemical compounds being in a specific ratio of about 60:40, it is typically considered a "solvent" rather than a mixture of compounds. This is because the 5-hydroxy-1,3-dioxane and 4-hydroxymethyl-1,3-dioxolane are in equilibrium with each other. Accordingly, the term glycerol formal (i.e., a mixture of 5-hydroxy-1,3-dioxane and 4-hydroxymethyl-1,3-dioxolane in a ratio of about 60:40), as used herein, is an organic solvent.

The term "oligonucleotide," as used herein, means at least two oligonucleotide bases connected by a phosphodiester linkage. In one embodiment, the oligonucleotide is a small double-stranded or single-stranded segment of DNA or RNA, typically about 5-50 nucleotides in length. In one embodiment, the oligonucleotide is about 5-45 nucleotide bases in length. In one embodiment, the oligonucleotide is about 5-30 nucleotide bases in length. In one embodiment, the oligonucleotide is about 10-50 nucleotide bases in length. In one embodiment, the oligonucleotide is about 10-45 nucleotide bases in length. In one embodiment, the oligonucleotide is about 10-30 nucleotide bases in length. In one embodiment, the oligonucleotide is about 20-50 nucleotide bases in length. In one embodiment, the oligonucleotide is about 20-45 nucleotide bases in length. In one embodiment, the oligonucleotide is about 20-30 nucleotide bases in length. The term "protonated oligonucleotide," as used herein, means an oligonucleotide wherein at least one of the phosphate groups of the oligonucleotide is protonated. In one embodiment, all of the phosphate groups of the oligonucleotide are protonated.

The term "aptamer," as used herein, means an oligonucleotide, which can be synthetic or natural, which can bind to a particular target molecule, such as a protein or metabolite, other than by Watson-Crick base pairing and have a pharmacological effect in an animal. Aptamers can be synthesized using conventional phosphodiester linked nucleotides and synthesized using standard solid or solution phase synthesis techniques which are known to those skilled in the art (See, for example, U.S. Pat. Nos. 5,475,096 and 5,270,163). The binding of aptarners to a target polypeptide can be readily tested by assays known to those skilled in the art (See, Burmeister et al., *Chem. Biol.*, 12: 25-33 (2005), U.S. Pat. No. 5,270,163, and U.S. Pat. No. 5,595,877). The term "protonated aptamer," as used herein, means an aptamer wherein at least one of the phosphate groups of the aptamer is protonated. In one embodiment, all of the phosphate groups of the aptamer are protonated.

The term "siRNA," as used herein means an oligonucleotide, which can be synthetic or natural, which can bind to another nucleotide sequence, such as that of messenger RNA, by Watson-Crick base pairing and have a pharmacological effect in an animal. SiRNA can also be synthesized using conventional phosphodiester linked nucleotides and synthesized using standard solid or solution phase synthesis techniques which are known to those skilled in the art (See, for example, U.S. Pat. Nos. 7,056,704 and 7,078,196). The identification of siRNA that will bind to a target nucleic acid sequence can be readily determined by methods known to those skilled in the art (See, for example, *Pharmacogenomics*, 6(8):879-83 (December 2005), *Nat. Chem. Biol.*, 2(12): 711-9 (December 2006), *Appl Biochem. Biotechnol.*, 119(1): 1-12 (October 2004)). The term "protonated siRNA," as used herein, means siRNA wherein at least one of the phosphate groups of the siRNA is protonated. In one embodiment, all of the phosphate groups of the siRNA are protonated.

The term "antisense nucleic acid," as that term is used herein, means a non-enzymatic nucleic acid molecule that binds to target RNA by means of RNA-RNA or RNA-DNA or RNA-PNA (protein nucleic acid; Egholm et al., *Nature*, 365 (1993) 566) interactions and alters the activity of the target RNA (for a review, see, Stein and Cheng, *Science*, 261 (1993) 1004 and U.S. Pat. No. 5,849,902). For a review of current antisense strategies, see, Schmajuk et al., *J. Biol. Chem.*, 274 (1999) 21783-21789, Delihas et al., *Nature*, 15 (1997) 751-753, Stein et al., *Antisense N. A. Drug Dev.*, 7 (1997) 151, Crooke, *Methods Enzymol.*, 313 (2000) 3-45; Crooke, *Biotech. Genet. Eng. Rev.*, 15 (1998) 121-157, and Crooke, *Ad. Pharmacol*, 40 (1997) 1-49). The identification of an antisense nucleic acid that will bind to a target nucleic acid sequence can be readily determined by methods known to those skilled in the art (See, for example, U.S. Pat. No. 5,639,595, U.S. Pat. No. 5,686,242, N. M. Dean, *Functional genomics and target validation approaches using antisense oligonucleotides technology, Curr. Opin. Biotechnol.*, 12(6):622-5 (2001), R. S. Geary et al., *Pharmacokinetics of phosphorothioate antisense oligodeoxynucleotides. Curr. Opin. Investig. Drugs*, 2(4):562-573 (2001), S. T. Crooke, *Progress in antisense technology: The end of the beginning, Methods Enzymol.*, 313 (*Antisense Technology*, Part A): 3-45 (2000), and S. T. Crooke, *Antisense Therapeutics, Biotechnol Genet Eng Rev.* 15:121-57 (1998). The term "protonated antisense nucleic acid," as used herein, means an antisense nucleic acid wherein at least one of the phosphate groups of the antisense nucleic acid is protonated. In one embodiment, all of the phosphate groups of the antisense nucleic acid are protonated.

The term "phospholipid," as used herein, means a compound having the general formula:

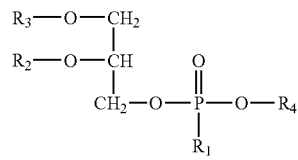

wherein $R_1$ is $O^-$ or —OH;

$R_2$ is:

(i) —H, or (ii) a $C_2$-$C_{36}$ saturated or unsaturated, linear or branched acyl group;

$R_3$ is:

(i) —H, (ii) a $C_2$-$C_{36}$ saturated or unsaturated, linear or branched acyl group; or (iii) —C=C—$R_9$ wherein $R_9$ is a $C_1$-$C_{22}$ saturated or unsaturated, linear or branched hydrocarbon group, optionally substituted with one or more nitrogen containing groups;

and at least one of $R_2$ or $R_3$ is not —H;

$R_4$ is:

(i) —H;

(ii) —$(CH_2)_n$—$R_5$, wherein $R_5$ is —$N(R_6)(R_7)$ or —$N^+(R_6)(R_7)(R_8)$, $R_6$, $R_7$, and $R_8$ are each independently —H, $C_1$-$C_3$ alkyl group, or $R_6$ and $R_7$ are connected to form a 5- or 6-membered heterocyclic ring with the nitrogen, and n is an integer ranging from 1 to 4, preferably 2;

(iii)

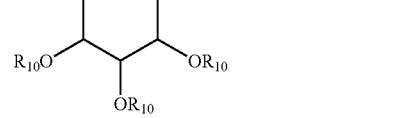

(iv)

wherein each $R_{10}$ is independently —H or —P(O)(OH)$_2$; or (v) —$CH_2CH(OH)CH_2(OH)$.

The term "saturated or unsaturated, linear or branched $C_2$-$C_{36}$ acyl group," as used herein, means a group of formula —O—C(O)—R, wherein R is a $C_1$-$C_{35}$ hydrocarbon group that can be saturated or unsaturated, linear or branched.

The term "sphingomyelin," as used herein, means a compound having the general formula:

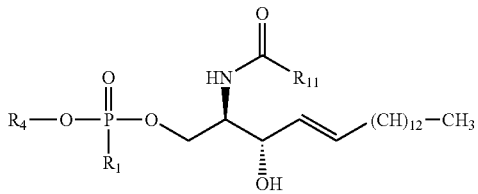

wherein
$R_1$ is O— or —OH;
$R_4$ is:
(i) —H; or
(ii) —(CH$_2$)$_n$—R$_5$,
  wherein $R_5$ is —N($R_6$)($R_7$) or —N$^+$($R_6$)($R_7$)($R_8$),
  $R_6$, $R_7$, and $R_8$ are each independently —H, $C_1$-$C_3$ alkyl, or $R_6$ and $R_7$ are connected to form a 5- or 6-membered heterocyclic ring with the nitrogen, and
  n is an integer ranging from 1 to 4, preferably 2; and
$R_{11}$ is a $C_1$-$C_{22}$ saturated or unsaturated, linear or branched hydrocarbon group optionally substituted with one or more nitrogen containing groups.

6.2 The Amino-acid-vitamin Ester

The amino acid-vitamin esters are esters formed between an amino acid and a vitamin that contains a hydroxyl group, i.e., an amino acid wherein the carboxylic acid group of the amino acid is esterified with the hydroxyl group (i.e., —OH group) of the vitamin. Accordingly, the amino acid-vitamin esters have the general formula (I):

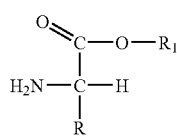

(I)

wherein
R is the amino acid side chain; and
O—$R_1$ is the residue of a vitamin.

As one of ordinary skill in the art would readily know, a wide variety of groups are possible for the amino acid side, R. For example, the amino acid side can be a hydrocarbon group that can be optionally substituted. Suitable substituents include, but are not limited to, halo, nitro, cyano, thiol, amino, hydroxy, carboxylic acid, sulfonic acid, aromatic group, and aromatic or non-aromatic heterocyclic group. Preferably the amino acid side chain is a $C_1$-$C_{10}$ straight or branched chain hydrocarbon, optionally substituted with a thiol, amino, hydroxy, carboxylic acid, aromatic group, or non-aromatic heterocyclic group; an aromatic group, or an aromatic or non-aromatic heterocyclic group.

The amino acid of the amino acid-vitamin ester can be a naturally occurring amino acid or a synthetically prepared amino acid. The amino acid can be a D-amino acid or an L-amino acid. Preferably, the amino acid-vitamin ester is the ester of a naturally occurring amino acid. More preferably, the amino acid-vitamin ester is an ester of an amino acid selected from glycine, alanine, valine, leucine, isoleucine, phenylalanine, asparagine, glutamine, tryptophane, proline, serine, threonine, tyrosine, hydroxyproline, cysteine, methionine, aspartic acid, glutamic acid, lysine, arginine, and histidine.

The vitamin can be any vitamin that includes a hydroxyl group. Illustrative vitamins include, but are not limited to, vitamin A (retinol), vitamin $B_1$ (thiamin), vitamin $B_2$ (riboflavin), vitamin $B_5$ (pantothenic acid), vitamin $B_6$, vitamin $B_{12}$ (cyanocobalamin), vitamin C, vitamin D, and vitamin E.

In one embodiment, the vitamin is vitamin A.
In one embodiment, the vitamin is vitamin $B_1$.
In one embodiment, the vitamin is vitamin $B_2$.
In one embodiment, the vitamin is vitamin $B_5$.
In one embodiment, the vitamin is vitamin $B_6$.
In one embodiment, the vitamin is vitamin $B_{12}$.
In one embodiment, the vitamin is vitamin C.
In one embodiment, the vitamin is vitamin D.
In one embodiment, the vitamin is vitamin E.

The amino acid-vitamin esters can be obtained by esterifying an amino acid with a vitamin of formula $R_1$—OH using methods well known to those skilled in the art such as those described in J. March, *Advanced Organic Chemistry, Reaction Mechanisms and Structure*, 4$^{th}$ ed. John Wiley & Sons, NY, 1992, pp. 393-400. The amino acids and vitamins are commercially available or can be prepared by methods well known to those skilled in the art. When esterifying the amino acid with the vitamin, it may be necessary to protect some other functional group of the amino acid or the vitamin with a protecting group that is subsequently removed after the esterification reaction. One of ordinary skill in the art would readily know what functional groups would need to be protected before esterifying the amino acid with the vitamin. Suitable protecting groups are known to those skilled in the art such as those described in T. W. Greene, et al. *Protective Groups in Organic Synthesis*, 3$^{rd}$ ed. (1999).

6.3 The Carboxylic Acid

The carboxylic acid can be any pharmaceutically acceptable carboxylic acid. Typically, the carboxylic acid is a $C_1$-$C_{22}$ carboxylic acid. Suitable carboxylic acids include, but are not limited to, acetic acid, propanic acid, butanoic acid, pentanoic acid, decanoic acid, hexanoic acid, benzoic acid, caproic acid, lauric acid, myristic acid, palmitic acid, stearic acid, palmic acid, oleic acid, linoleic acid, and linolenic acid.

In one embodiment, the carboxylic acid is a $C_1$-$C_{12}$ carboxylic acid.
In one embodiment, the carboxylic acid is a $C_1$-$C_{10}$ carboxylic acid.
In one embodiment, the carboxylic acid is a $C_1$-$C_6$ carboxylic acid.
In one embodiment, the carboxylic acid is a $C_1$-$C_3$ carboxylic acid.
In one embodiment, the carboxylic acid is a $C_6$-$C_{22}$ carboxylic acid.
In one embodiment, the carboxylic acid is a $C_8$-$C_{22}$ carboxylic acid.
In one embodiment, the carboxylic acid is a $C_{10}$-$C_{22}$ carboxylic acid.
In one embodiment, the carboxylic acid is a $C_6$-$C_{18}$ carboxylic acid.
In one embodiment, the carboxylic acid is a $C_8$-$C_{18}$ carboxylic acid.
In one embodiment, the carboxylic acid is a $C_{10}$-$C_{18}$ carboxylic acid.
In one embodiment, the carboxylic acid is a saturated or unsaturated fatty acid.
In one embodiment, the carboxylic acid is a saturated fatty acid.

In one embodiment, the carboxylic acid is an unsaturated fatty acid.

In one embodiment, the carboxylic acid is a dicarboxylic acid. Suitable dicarboxylic acids include, but are not limited to, oxalic acid, malonic aid, succinic acid, glutamic acid, adipic acid, and pimelic acid.

In one embodiment, the carboxylic acid is hyaluronic acid.

The carboxylic acids are commercially available or can be prepared by methods well known to those skilled in the art.

In one embodiment, the carboxylic acid is an N-acyl amino acid. The N-acyl amino acids have the following general formula (II):

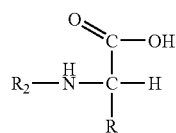

(II)

wherein

R is the amino acid side chain and is defined above; and $R_2$ is an acyl group of formula —C(O)—$R_5$, wherein $R_5$ is a substituted $C_1$ to $C_{21}$ hydrocarbon group, i.e., the acyl group, $R_2$, is a $C_1$- to $C_{22}$ acyl group. Representative acyl groups of formula —C(O)—$R_5$ include, but are not limited to, acetyl, propionyl, butanoyl, hexanoyl, caproyl, heptoyl, octoyl, nonoyl, decoyl, undecoyl, dodecoyl, tridecoyl, tetradecoyl, pentadecoyl, hexadecoyl, heptadecoyl, octadecoyl, laurolyl, myristoyl, palmitoyl, stearoyl, palmioleoyl, oleoyl, linoleoyl, linolenoyl, and benzoyl.

In one embodiment, $R_5$ is a $C_5$-$C_2$, hydrocarbon group, i.e., the acyl group of formula —C(O)—$R_5$ is a $C_6$-$C_{22}$ acyl group.

In one embodiment, $R_5$ is a $C_7$-$C_{21}$ hydrocarbon group, i.e., the acyl group of formula —C(O)—$R_5$ is a $C_8$-$C_{22}$ acyl group.

In one embodiment, $R_5$ is a $C_9$-$C_2$, hydrocarbon group, i.e., the acyl group of formula —C(O)—$R_5$ is a $C_{10}$-$C_{22}$ acyl group.

In one embodiment, $R_5$ is a $C_5$-$C_{17}$ hydrocarbon group, i.e., the acyl group of formula —C(O)—$R_5$ is a $C_6$-$C_{18}$ acyl group.

In one embodiment, $R_5$ is a $C_7$-$C_{17}$ hydrocarbon group, i.e., the acyl group of formula —C(O)—$R_5$ is a $C_8$-$C_{18}$ acyl group.

In one embodiment, $R_5$ is a $C_9$-$C_{17}$ hydrocarbon group, i.e., the acyl group of formula —C(O)—$R_5$ is a $C_{10}$-$C_{18}$ acyl group.

In one embodiment, the acyl group of formula —C(O)—$R_5$ is obtained from a saturated or unsaturated fatty acid.

In one embodiment, the acyl group of formula —C(O)—$R_5$ is a caproyl, laurolyl, myristoyl, palmitoyl, stearoyl, palmioleoyl, oleoyl, linoleoyl, or linolenoyl group.

The N-acyl amino acids can be obtained by methods well known to those skilled in the art. For example, the N-acyl amino acids can be obtained by reacting an amino acid with an acid halide of formula T-C(O)—$R_5$, wherein T is a halide, preferably chloride, and $R_5$ is as defined above, using methods well known to those skilled in the art. When N-acylating the amino acid with the acid halide of formula T-C(O)—$R_5$, it may be necessary to protect some other functional group of the amino acid or the acid halide with a protecting group that is subsequently removed after the acylation reaction. One of ordinary skill in the art would readily know what functional groups would need to be protected before acylating the amino acid with the acid halide of formula T-C(O)—$R_5$. Suitable protecting groups are known to those skilled in the art such as those described in T. W. Greene, et al. *Protective Groups in Organic Synthesis*, 3$^{rd}$ ed. (1999).

Acid halides can be obtained using methods well known to those skilled in the art such as those described in J. March, *Advanced Organic Chemistry, Reaction Mechanisms and Structure*, 4$^{th}$ ed. John Wiley & Sons, NY, 1992, pp. 437-8. For example, acid halides can be prepared by reacting a carboxylic acid with thionyl chloride, bromide, or iodide. Acid chlorides and bromides can also be prepared by reacting a carboxylic acid with phosphorous trichloride or phosphorous tribromide, respectively. Acid chlorides can also be prepared by reacting a carboxylic acid with $Ph_3P$ in carbon tetrachloride. Acid fluorides can be prepared by reacting a carboxylic acid with cyanuric fluoride.

6.4 The Pharmaceutically Acceptable Organic Solvent

Any pharmaceutically acceptable organic solvent can be used in the pharmaceutical compositions of the invention. Representative, pharmaceutically acceptable organic solvents include, but are not limited to, pyrrolidone, N-methyl-2-pyrrolidone, polyethylene glycol, propylene glycol (i.e., 1,3-propylene glycol, 1,2-propylene glycol, or a mixture thereof), glycerol formal, isosorbide dimethyl ether, ethanol, dimethyl sulfoxide, tetraglycol, tetrahydrofurfuryl alcohol, triacetin, propylene carbonate, dimethyl acetamide, dimethyl formamide, dimethyl sulfoxide, and combinations thereof.

In one embodiment, the pharmaceutically acceptable organic solvent is a water soluble solvent. A representative pharmaceutically acceptable water soluble organic solvents is triacetin.

In one embodiment, the pharmaceutically acceptable organic solvent is a water miscible solvent. Representative pharmaceutically acceptable water miscible organic solvents include, but are not limited to, glycerol formal, polyethylene glycol, and propylene glycol.

In one embodiment, the pharmaceutically acceptable organic solvent comprises pyrrolidone. In one embodiment, the pharmaceutically acceptable organic solvent is pyrrolidone substantially free of another organic solvent.

In one embodiment, the pharmaceutically acceptable organic solvent comprises N-methyl-2-pyrrolidone. In one embodiment, the pharmaceutically acceptable organic solvent is N-methyl-2-pyrrolidone substantially free of another organic solvent.

In one embodiment, the pharmaceutically acceptable organic solvent comprises polyethylene glycol. In one embodiment, the pharmaceutically acceptable organic solvent is polyethylene glycol substantially free of another organic solvent.

In one embodiment, the pharmaceutically acceptable organic solvent comprises propylene glycol. In one embodiment, the pharmaceutically acceptable organic solvent is propylene glycol substantially free of another organic solvent. In one embodiment, the pharmaceutically acceptable organic solvent comprises 1,2-propylene glycol. In one embodiment, the pharmaceutically acceptable organic solvent is 1,2-propylene glycol substantially free of another organic solvent. In one embodiment, the pharmaceutically acceptable organic solvent comprises 1,3-propylene glycol. In one embodiment, the pharmaceutically acceptable organic solvent is 1,3-propylene glycol substantially free of another organic solvent. In one embodiment, the pharmaceutically acceptable organic solvent comprises a mixture of 1,2-propylene glycol and 1,3-propylene glycol. In one embodiment, the pharmaceutically acceptable organic solvent is a mixture of 1,2-propylene glycol and 1,3-propylene glycol substantially free of another organic solvent.

In one embodiment, the pharmaceutically acceptable organic solvent comprises glycerol formal. In one embodiment, the pharmaceutically acceptable organic solvent is glycerol formal substantially free of another organic solvent.

In one embodiment, the pharmaceutically acceptable organic solvent comprises isosorbid dimethyl ether. In one embodiment, the pharmaceutically acceptable organic solvent is isosorbid dimethyl ether substantially free of another organic solvent.

In one embodiment, the pharmaceutically acceptable organic solvent comprises ethanol. In one embodiment, the pharmaceutically acceptable organic solvent is ethanol substantially free of another organic solvent.

In one embodiment, the pharmaceutically acceptable organic solvent comprises dimethyl sulfoxide. In one embodiment, the pharmaceutically acceptable organic solvent is dimethyl sulfoxide substantially free of another organic solvent.

In one embodiment, the pharmaceutically acceptable organic solvent comprises tetraglycol. In one embodiment, the pharmaceutically acceptable organic solvent is tetraglycol substantially free of another organic solvent.

In one embodiment, the pharmaceutically acceptable organic solvent comprises tetrahydrofurfuryl alcohol. In one embodiment, the pharmaceutically acceptable organic solvent is tetrahydrofurfuryl alcohol substantially free of another organic solvent.

In one embodiment, the pharmaceutically acceptable organic solvent comprises triacetin. In one embodiment, the pharmaceutically acceptable organic solvent is triacetin substantially free of another organic solvent.

In one embodiment, the pharmaceutically acceptable organic solvent comprises propylene carbonate. In one embodiment, the pharmaceutically acceptable organic solvent is propylene carbonate substantially free of another organic solvent.

In one embodiment, the pharmaceutically acceptable organic solvent comprises dimethyl acetamide. In one embodiment, the pharmaceutically acceptable organic solvent is dimethyl acetamide substantially free of another organic solvent.

In one embodiment, the pharmaceutically acceptable organic solvent comprises dimethyl formamide. In one embodiment, the pharmaceutically acceptable organic solvent is dimethyl formamide substantially free of another organic solvent.

In one embodiment, the pharmaceutically acceptable organic solvent comprises a mixture of propylene glycol (which can be 1,2-propylene glycol, 1,3-propylene glycol, or a mixture thereof) and glycerol formal. In one embodiment, the pharmaceutically acceptable organic solvent is a mixture of propylene glycol (which can be 1,2-propylene glycol, 1,3-propylene glycol, or a mixture thereof) and glycerol formal substantially free of another organic solvent.

In one embodiment, the pharmaceutically acceptable organic solvent is about 10 percent propylene glycol (which can be 1,2-propylene glycol, 1,3-propylene glycol, or a mixture thereof) in glycerol formal.

In one embodiment, the pharmaceutically acceptable organic solvent is a solvent that is recognized as GRAS by the FDA for administration or consumption by animals.

In one embodiment, the pharmaceutically acceptable organic solvent is a solvent that is recognized as GRAS by the FDA for administration or consumption by humans.

In one embodiment, the pharmaceutically acceptable organic solvent is substantially free of water. Pharmaceutically acceptable organic solvents that are substantially free of water are advantageous since they are not conducive to bacterial growth. Accordingly, it is typically not necessary to include a preservative in pharmaceutical compositions that are substantially free of water.

6.5 The Pharmaceutically Active Compound

Examples of pharmaceutically active agents useful in the composition and methods of the invention include, but are not limited to, α-adrenergic agonists, β-adrenergic agonists, α-adrenergic blockers, β-adrenergic blockers, aldose reductase inhibitors, anabolics, analgesics (narcotic and non-narcotic), androgens, anesthetics, anorexics, anthelmintics (e.g., cestode, nematode, onchocerca, schistosoma, and the like), anti-allergics, anti-ameboics, anti-androgens, anti-anginals, anti-arrhythmics, anti-arteriosclerotics, anti-arthritics, antibiotics and other antibacterials, anti-cholinergics, anti-convulsants, anti-depressants, anti-diabetics agents, anti-diarrheals, anti-diuretics, anti-estrogens, antifungals, anti-glaucomas, anti-gonadotropins, anti-gout agents, anti-histaminics, anti-hyperlipoproteinemics, anti-hypertensives, anti-hyperthyroid agents, anti-hypertrophy agents, anti-hypotensives, anti-hypothyroid agents, anti-inflammatories, anti-malarials, antimicrobials, anti-migraine agents, anti-nausea agents, anti-neoplastics, antioxidants, antiparasitic agents, anti-parkinsonian agents, anti-pheochromocytoma agents, anti-pneumocytes agents, antiproliferative agents, anti-protozoals (e.g., leishmania, trichomonas, trypansoma, and the like), anti-pruritic agents, anti-psoratic agents, anti-psychotic agents, anti-pyretics, anti-rheumatics, anti ricketts agents, anti-seborrheic agents, antiseptics, anti-spasmodic agents, anti-thrombotic agents, antitussives, anti-ulcer agents, anti-urolithic agents, anti-venins, antivirals, anxiolytics, benzodiazepine antagonists, bronchodilators, calcium channel blockers, calcium regulators, cardiotonics, chelating agents, chemotherapeutics, cholecystokinin antagonists, cholelitholytic agents, choleretics, cholinergics, cholinesterase inhibitors, cholinesterase reactivators, central nervous system stimulants and agents, decongestants, diuretics, dopamine receptor agonists, drugs for treating or preventing pain, ectoparasiticides, enzymes, enzyme inducers, estrogens, gastric secretion inhibitors, glucocorticoids, gonad-stimulating principles, gonadotropic hormones, growth hormones, growth hormone releasing factors, growth stimulants, hemolytics, heparin agonists, hepatoprotectants, hypnotics, immune system boosters, immunomodulators, immunosuppressants, lactation stimulating hormones, LH-RH stimulating agonists, lipotropics, lupus erythmatosus suppressants, mineral corticoids, miotics, monoamine oxidase inhibitors, mucolytics, muscle relaxants, narcotic antagonists, neuroprotectives, neotropics, ovarian hormones, oxytocics, pepsin inhibitors, peristaltic stimulators, progestrogens, prolactin inhibitors, protoglandins, prostoglandin analogs, protease inhibitors, respiratory stimulants, sclerosing agents, sedatives, steroids, thrombolytics, thyrotropic hormones, transdermal penetration enhancers, uricosurics, vasoconstrictors, vasodilators (e.g., cerebral, coronary, peropheral, and the like), vasoprotectants, vitamins, vitamin source extracts, vulneraries (including, but not limited to, those listed in U.S. Pat. No. 5,719,197, the entire disclosure of which is incorporated herein by reference), and combinations thereof. Other additionally or alternately acceptable pharmaceutically active agents can be found, e.g., in U.S. Pat. No. 6,221,383, the entire disclosure of which is incorporated herein by reference.

In one embodiment, the pharmaceutically active compound is an antibacterial agent. Examples of useful antibacterial agents include, but are not limited to, β-lactam antibiotics such as penicillins, amoxicillin, ampicillin, and cephalosporins; macrolide antibiotics such as oleandomycin and erythromycin; tetracyclines such as tetracycline, oxytetracycline, and chlortetracycline; procaine penicillin G; quinolones such as nalidixic acid and norfloxacin; sulfonamides; chloramphenicol; florfenicol; thiamphenicol; aminoglycosides such as streptomycin, kanamycin, and gentamycins; nucleoside antibiotics such as polyoxin B; actinorhodine; bacitracin; candicidin A; ceftiofor; clindamycin; cycloheximide; cycloserine; fosfomycin; griseofulvin; metronidazole; monensin; novobiocin; rifampin; streptothricin; tetranactin; tilmicosin; tylosin; actinomycin D; adriamycin; bleomycin B2; glycolipids such as moenomycin A; mitomycin C; nojirimycin; valinomycin; and vancomycin; (See, e.g., Bradford P. Smith, *Large Animal Internal Medicine,* 2nd edn., Mosby, St. Louis, 1996, p. 644, and S. Birchard and R. Sherding, *Saunders Manual of Small Animal Practice, W.B. Saunders Company, Philadelphia,* 1994, p. 739).

In one embodiment, the pharmaceutically active compound is an antifungal agent. Examples of useful antifungal agents include, but are not limited to terbinafine, amphotericin B, ketaconazole, miconazole, 5-fluorocytosine, enilconazole, itraconazole, thiabendazole, and iodides (See, e.g., Bradford P. Smith, *Large Animal Internal Medicine,* 2nd edn., Mosby, St. Louis, 1996, p. 576, and S. Birchard and R. Sherding, *Saunders Manual of Small Animal Practice*, W.B. Saunders Company, Philadelphia, 1994, p. 576).

In one embodiment, the pharmaceutically active compound is an antiviral agent. Examples of useful antiviral agents include, but are not limited to, interferon and adefovir (See, e.g., Bradford P. Smith, *Large Animal Internal Medicine,* 2nd edn., Mosby, St. Louis, 1996, p. 646).

In one embodiment, the pharmaceutically active compound is an antiparasitic agent. Examples of useful antiparasitic agents include, but are not limited to, benzimidazoles, such as thiabendazole, fenbendazole, mebendazole, oxfendazole, oxibendazole, albendazole, parbendazole, and febantel; tetrahydropyridines such as morantel tartrate/pyrantel pamoate; levamisole, organophosphates such as haloxon, coumaphos, trichlorfon, and dichlorvos; piperazine salts; ivermectin; and phenothiazine (See, e.g., Bradford P. Smith, *Large Animal Internal Medicine,* 2nd edn., Mosby, St. Louis, 1996, p. 1688).

In one embodiment, the pharmaceutically active compound is an anti-inflammatory agent. Examples of useful anti-inflammatory agents include, but are not limited to, steroids such as betamethazone; corticosteroids such as dexamethasone; antihistamines; and non-steroidal anti-inflammatory drugs such as aspirin, flunixin meglumine, phenylbutazone, diclofenac, naproxen, ketoprofen, carprofen, and ibuprofin (See, e.g., Bradford P. Smith, *Large Animal Internal Medicine,* 2nd edn., Mosby, St. Louis, 1996, p. 645).

In one embodiment, the pharmaceutically active compound is a protein.

In one embodiment, the pharmaceutically active compound is a hormone.

In one embodiment, the pharmaceutically active compound is a peptide.

In one embodiment, the pharmaceutically active compound is insulin.

In one embodiment, the pharmaceutically active compound is an anti-depressant.

In one embodiment, the pharmaceutically active compound is fluoxetine.

In one embodiment, the pharmaceutically active compound is carprofen.

In one embodiment, the pharmaceutically active compound is flunixin.

One of ordinary skill in the art will readily recognize what pharmaceutically active compounds are acidic pharmaceutically active compounds, what pharmaceutically active compounds are neutral non-acidic pharmaceutically active compounds, and what pharmaceutically active compounds are pharmaceutically acceptable salts of pharmaceutically active compounds.

6.6 The Oligonucleotide

The oligonucleotide can be any oligonucleotide known to those skilled in the art.

In one embodiment, the oligonucleotide is a DNA strand. In one embodiment, the DNA is double stranded DNA. In one embodiment, the DNA is single stranded DNA.

In one embodiment, the oligonucleotide is an RNA strand.

In one embodiment, the oligonucleotide is an aptamer.

In one embodiment, the oligonucleotide is an siRNA.

In one embodiment, the oligonucleotide is an antisense nucleic acid.

In one embodiment, the oligonucleotide has a molecular weight of up to 80 kD.

In one embodiment, the molecular weight of the oligonucleotide ranges from about 15 kD to 80 kD. In one embodiment, the molecular weight of the oligonucleotide ranges from about 10 kD to 80 kD. In one embodiment, the molecular weight of the oligonucleotide ranges from about 5 kD to 80 kD.

In one embodiment, the oligonucleotide has a molecular weight of up to 60 kD. In one embodiment, the molecular weight of the oligonucleotide ranges from about 15 kD to 60 kD. In one embodiment, the molecular weight of the oligonucleotide ranges from about 10 kD to 60 kD. In one embodiment, the molecular weight of the oligonucleotide ranges from about 5 kD to 60 kD.

In one embodiment, the oligonucleotide has a molecular weight of up to 40 kD. In one embodiment, the molecular weight of the oligonucleotide ranges from about 15 kD to 40 kD. In one embodiment, the molecular weight of the oligonucleotide ranges from about 10 kD to 40 kD. In one embodiment, the molecular weight of the oligonucleotide ranges from about 5 kD to 40 kD.

In one embodiment, the oligonucleotide has a molecular weight of up to 30 kD. In one embodiment, the molecular weight of the oligonucleotide ranges from about 15 kD to 30 kD. In one embodiment, the molecular weight of the oligonucleotide ranges from about 10 kD to 30 kD. In one embodiment, the molecular weight of the oligonucleotide ranges from about 5 kD to 30 kD.

In one embodiment, the oligonucleotide has a molecular weight of more than 20 kD. In one embodiment, the molecular weight of the oligonucleotide ranges from about 15 kD to 20 kD. In one embodiment, the molecular weight of the oligonucleotide ranges from about 10 kD to 20 kD. In one embodiment, the molecular weight of the oligonucleotide ranges from about 5 kD to 20 kD.

In one embodiment, the molecular weight of the oligonucleotide ranges from about 5 kD to 10 kD.

The nucleotides that make up the oligonucleotide can be modified to, for example, improve their stability, i.e., improve their in vivo half-life, and/or to reduce their rate of excretion when administered to an animal. The term "modified" encompasses nucleotides with a covalently modified base and/or sugar. For example, modified nucleotides include nucleotides having sugars which are covalently attached to low molecular weight organic groups other than a hydroxyl group at the 3' position and other than a phosphate group at the 5' position. Modified nucleotides may also include 2' substituted sugars such as 2'-O-methyl-; 2'-O-alkyl; 2'-O-allyl; 2'-S-alkyl; 2'-S-allyl; 2'-fluoro-; 2'-halo or 2'-azido-ribose; carbocyclic sugar analogues; α-anomeric sugars; and epimeric sugars such as arabinose, xyloses or lyxoses, pyranose sugars, furanose sugars, and sedoheptulose.

Modified nucleotides are known in the art and include, but are not limited to, alkylated purines and/or pyrimidines; acylated purines and/or pyrimidines; or other heterocycles. These classes of pyrimidines and purines are known in the art and include, pseudoisocytosine; N4, N4-ethanocytosine; 8-hydroxy-N-6-methyladenine; 4-acetylcytosine, 5-(carboxyhydroxylmethyl)uracil; 5-fluorouracil; 5-bromouracil; 5-carboxymethylaminomethyl-2-thiouracil; 5-carboxymethylaminomethyl uracil; dihydrouracil; inosine; N6-isopentyl-adenine; 1-methyladenine; 1-methylpseudouracil; 1-methylguanine; 2,2-dimethylguanine; 2-methyladenine; 2-methylguanine; 3-methylcytosine; 5-methylcytosine; N6-methyladenine; 7-methylguanine; 5-methylaminomethyl uracil; 5-methoxy amino methyl-2-thiouracil; β-D-mannosylqueosine; 5-methoxycarbonylmethyluracil; 5-methoxyuracil; 2 methylthio-N-6-isopentenyladenine; uracil-5-oxyacetic acid methyl ester; psueouracil; 2-thiocytosine; 5-methyl-2 thiouracil, 2-thiouracil; 4-thiouracil; 5-methyluracil; N-uracil-5-oxyacetic acid methylester; uracil 5-oxyacetic acid; queosine; 2-thiocytosine; 5-propyluracil; 5-propylcytosine; 5-ethyluracil; 5-ethylcytosine; 5-butyluracil; 5-pentyluracil; 5-pentylcytosine; and 2,6-diaminopurine; methylpseudouracil; 1-methylguanine; and 1-methylcytosine.

The oligonucleotide can also be modified by replacing one or more phosphodiester linkages with alternative linking groups. Alternative linking groups include, but are not limited to embodiments wherein P(O)O is replaced by P(O)S, P(S)S, P(O)NR$_2$, P(O)R, P(O)OR', CO, or CH$_2$, wherein each R or R' is independently H or a substituted or unsubstituted C$_1$-C$_{20}$ alkyl. A preferred set of R substitutions for the P(O)NR$_2$ group are hydrogen and methoxyethyl. Linking groups are typically attached to each adjacent nucleotide through an —O— bond, but may be modified to include —N— or —S— bonds. Not all linkages in an oligomer need to be identical.

The oligonucleotide can also be modified by conjugating the oligonucleotide to a polymer, for example, to reduce the rate of excretion when administered to an animal. For example, the oligonucleotide can be "PEGylated," i.e., conjugated to polyethylene glycol ("PEG"). In one embodiment, the PEG has an average molecular weight ranging from about 20 kD to 80 kD. Methods to conjugate an oligonucleotide, specifically an aptamer, with a polymer, such PEG, are well known to those skilled in the art (See, e.g., Greg T. Hermanson, *Bioconjugate Techniques*, Academic Press, 1966)

In one embodiment, the oligonucleotide is conjugated to a polymer.

In one embodiment, the oligonucleotide is an RNA strand that has been conjugated to a polymer.

In one embodiment, the oligonucleotide is an DNA strand that has been conjugated to a polymer.

In one embodiment, the oligonucleotide is conjugated to PEG.

In one embodiment, the oligonucleotide is an RNA strand that has been conjugated to PEG.

In one embodiment, the oligonucleotide is an DNA strand that has been conjugated to PEG.

In one embodiment, the oligonucleotide is a RNA strand wherein at least one of the 2'-hydroxyls on the sugars that make up the oligonucleotide are O-methylated.

In one embodiment, the oligonucleotide is a RNA strand wherein at least one of the 2'-hydroxyls on the sugars that make up the oligonucleotide are O-methylated and wherein the RNA strand has been conjugated to a polymer.

In one embodiment, the oligonucleotide is a RNA strand wherein at least one of the 2'-hydroxyls on the nucleotides that make up the oligonucleotide are O-methylated and wherein the RNA strand has been conjugated to PEG.

In one embodiment, the oligonucleotide is an aptamer that binds to VEGF (vascular endothelial growth factor).

As an example of a modified aptamer useful in the compositions and methods of the invention see P. Burmeister et al., *Direct In Vitro Selection of a 2'-O-methyl Aptamer to VEGF, Chemistry and Biology*, vol. 12, 25-33, January 2005.

In one embodiment, the aptamer is ARC224 identified in P. Burmeister et al., *Direct In Vitro Selection of a 2'-O-methyl Aptamer to VEGF, Chemistry and Biology*, vol. 12, 25-33, January 2005.

In one embodiment, the aptamer is ARC245 identified in P. Burmeister et al., *Direct In Vitro Selection of a 2'-O-methyl Aptamer to VEGF, Chemistry and Biology*, vol. 12, 25-33, January 2005.

In one embodiment, the aptamer is ARC225 identified in P. Burmeister et al., *Direct In Vitro Selection of a 2'-O-methyl Aptamer to VEGF, Chemistry and Biology*, vol. 12, 25-33, January 2005.

In one embodiment, the aptamer is ARC259 identified in P. Burmeister et al., *Direct In Vitro Selection of a 2'-O-methyl Aptamer to VEGF, Chemistry and Biology*, vol. 12, 25-33, January 2005.

In one embodiment, the aptamer is ARC259 identified in P. Burmeister et al., *Direct In Vitro Selection of a 2'-O-methyl Aptamer to VEGF, Chemistry and Biology*, vol. 12, 25-33, January 2005 wherein the 5' phosphate group of the aptamer has been pegylated with:

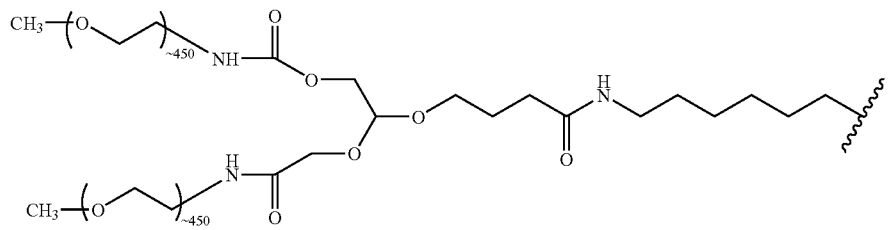

(referred to hereinafter as "pegylated ARC259").

6.7 The Pharmaceutical Compositions

6.7.1 Pharmaceutical Compositions Comprising (i) an Amino Acid-vitamin Ester (ii) an Acidic Pharmaceutically Active Compound The amino acid-vitamin ester can be any of the amino acid-vitamin esters described above.

The acidic pharmaceutically active compound can be any acidic pharmaceutically active compound.

In one embodiment, the acidic pharmaceutically active compound is an anti-inflammatory selected from aspirin, flunixin, diclofenac, naproxen, ketoprofen, carprofen, and ibuprofen.

In one embodiment, the pharmaceutically active compound is flunixin.

In one embodiment, the pharmaceutically active compound is diclofenac.

In one embodiment, the pharmaceutically active compound is naproxen.

In one embodiment, the pharmaceutically active compound is ketoprofen.

In one embodiment, the pharmaceutically active compound is carprofen.

In one embodiment, the pharmaceutically active compound is ibuprofen.

In one embodiment, the pharmaceutically active compound is a phosphorylated nucleotide such as adefovir.

In one embodiment, the pharmaceutical composition is a solid. Without wishing to be bound by theory, it is believed that the solid is a salt formed between the amino acid-vitamin ester and the acidic pharmaceutically active compound wherein the acidic pharmaceutically active compound protonates the α-amino group of the amino acid-vitamin ester.

In one embodiment, the pharmaceutical composition further comprises a pharmaceutically acceptable organic solvent.

The pharmaceutically acceptable organic solvent can be any pharmaceutically acceptable organic solvent described above.

In one embodiment, the pharmaceutical composition further comprising a solvent is a suspension of solid particles in the pharmaceutically acceptable organic solvent. Without wishing to be bound by theory, it is believed that the solid particles comprise a salt formed between the amino acid-vitamin ester and the acidic pharmaceutically active compound wherein the acidic pharmaceutically active compound protonates the α-amino group of the amino acid-vitamin ester.

In one embodiment, comprising a pharmaceutically acceptable organic solvent the pharmaceutical composition is injectable. In one embodiment, the pharmaceutical composition further comprising a pharmaceutically acceptable organic solvent is a solution. In one embodiment, comprising a pharmaceutically acceptable organic solvent the pharmaceutical composition is injectable and forms a precipitate when injected into water.

When the injectable pharmaceutical compositions are injected into water they form a precipitate. Without wishing to be bound by theory, it is believed that the α-amino group of the amino acid-vitamin ester is protonated by the acidic pharmaceutically active compound to form a salt that is soluble in the pharmaceutically acceptable organic solvent but insoluble in water. Accordingly, when the pharmaceutical compositions are injected into an animal, at least a portion of the pharmaceutical composition precipitates at the injection site to provide a drug depot. Without wishing to be bound by theory, it is believed that when the pharmaceutical compositions are injected into an animal, the pharmaceutically acceptable organic solvent diffuses away from the injection site and aqueous bodily fluids diffuse towards the injection site, resulting in an increase in concentration of water at the injection site, that causes at least a portion of the composition to precipitate and form a drug depot. The precipitate can take the form of a solid, a crystal, a gummy mass, or a gel. The precipitate, however, provides a depot of the pharmaceutically active compound at the injection site that releases the pharmaceutically active compound over time. Pharmaceutical compositions that are suspensions can also form drug depots when injected into an animal.

The molar ratio of acidic groups on the acidic pharmaceutically active compound to the amino acid-vitamin ester is typically about 1.5:1, preferably about 1.25:1, more preferably about 1.1:1. and most preferably about 1:1. Accordingly, when the acidic pharmaceutically active compound is a mono-protic carboxylic acid the molar ratio of the acidic pharmaceutically active compound to the amino acid-vitamin ester is about 1.5:1, preferably about 1.25:1, more preferably about 1.1:1, and most preferably about 1:1. When the acidic pharmaceutically active compound is a dicarboxylic acid, however, the ratio of the acidic pharmaceutically active compound to the amino acid-vitamin ester is typically about 0.75:1, preferably about 0.625:1, more preferably about 0.55:1, and most preferably about 0.5:1.

When the molar ratio of acidic groups on the acidic pharmaceutically active compound to the amino acid-vitamin ester is greater than 1, the pharmaceutical composition will also include the non-salt or free form of the acidic pharmaceutically active compound. Compositions further comprising the free form of the acidic pharmaceutically active compound provide an initial dose or "burst" of the acidic pharmaceutically active compound when administered to an animal. Accordingly, in some embodiments, the molar ratio of acidic groups on the acidic pharmaceutically active compound to the amino acid-vitamin ester is greater than 1 to provide a burst.

Typically, however, the pharmaceutical composition includes about 1 equivalent of amino acid-vitamin ester for each equivalent of acidic functional groups in the acidic pharmaceutically active compound so that there is substantially no free acidic pharmaceutically active compound. For example, if the acidic pharmaceutically active compound has a single acidic functional group, the acidic pharmaceutical composition includes about 1 equivalent of amino acid-vitamin ester for each equivalent of acidic pharmaceutically active compound. If the acidic pharmaceutically active compound, however, has two acidic functional group, the acidic pharmaceutical composition typically includes about 2 equivalent of amino acid-vitamin ester for each equivalent of acidic pharmaceutically active compound.

By varying the lipophilicity and/or molecular weight of the amino acid-vitamin ester it is possible to vary the rate at which the acidic pharmaceutically active compound is released from the drug depot. Generally, the more lipophilic the amino acid-vitamin ester, the more slowly drug is released. The lipophilicity and/or molecular weight of the amino acid-vitamin ester can be varied by varying the amino acid used to form the amino acid-vitamin ester. For example, the lipophilicity and/or molecular weight of the amino acid-vitamin ester can be varied by varying the R group of the amino acid or by varying the vitamin. For example, when R is a hydrocarbon group, the higher the molecular weight of R, the more lipophilic is the amino acid-vitamin ester.

The combined amount of the acidic pharmaceutically active compound and amino acid-vitamin ester in pharmaceutical compositions that further comprise a pharmaceutically acceptable organic solvent typically ranges from about 1 to 90 percent by weight of the pharmaceutical composition, preferably about 5 to 80 percent by weight of the pharmaceutical composition, more preferably about 7.5 to 70 percent by weight of the pharmaceutical composition, and most preferably about 10 to 60 by weight of the pharmaceutical composition.

One of ordinary skill in the art will recognize, however, that the amount of the acidic pharmaceutically active compound and amino acid-vitamin ester in the pharmaceutical composition can vary widely depending on the acidic pharmaceutically active compound, the amino acid-vitamin ester, and the solvent used in the pharmaceutical composition.

In one embodiment, the amino acid in the amino acid-vitamin ester is lysine (a "lysine-vitamin ester"). Without wishing to be bound by theory it is believed that the amino acid ester or amide of lysine cross-links two molecules of acidic pharmaceutically active compound as depicted below for an ester of lysine:

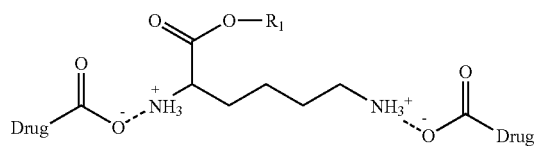

wherein $R_1$ has the meaning described above and Drug-C(O) O$^-$ is the acidic pharmaceutically active compound.

The molar ratio of acidic groups on the pharmaceutically active compound to amine groups on the lysine-vitamin ester typically ranges from about 1.5:1 to 1:1.5. In one embodiment, the molar ratio of acidic groups on the pharmaceutically active compound to amine groups on the lysine-vitamin ester ranges from about 1.25:1 to 1:1.25. In one embodiment, the molar ratio of acidic groups on the pharmaceutically active compound to amine groups on the lysine-vitamin ester ranges from about 1.1:1 to 1:1.1. In one embodiment, the molar ratio of acidic groups on the pharmaceutically active compound to amine groups on the lysine-vitamin ester is about 1:1.

In one embodiment, the molar ratio of amine groups on the lysine-vitamin ester to acidic groups on the pharmaceutically active compound is greater than about 1:1. In one embodiment, the molar ratio of amine groups on the lysine-vitamin ester relative to acidic groups on the pharmaceutically active compound is greater than about 2:1. In one embodiment, the molar ratio of amine groups on the lysine-vitamin ester relative to acidic groups on the pharmaceutically active compound is greater than about 5:1. In one embodiment, the molar ratio of amine groups on the lysine-vitamin ester relative to acidic groups on the pharmaceutically active compound is greater than about 8:1. In one embodiment, the molar ratio of amine groups on the lysine-vitamin ester relative to acidic groups on the pharmaceutically active compound is greater than about 10:1. In one embodiment, the molar ratio of amine groups on the lysine-vitamin ester relative to acidic groups on the pharmaceutically active compound is greater than about 12:1. In one embodiment, the molar ratio of amine groups on the lysine-vitamin ester relative to acidic groups on the pharmaceutically active compound ranges from about 2:1 to 5:1.

In one embodiment, the molar ratio of amine groups on the lysine-vitamin ester relative to acidic groups on the pharmaceutically active compound ranges from about 2:1 to 8:1. In one embodiment, the molar ratio of amine groups on the lysine-vitamin ester relative to acidic groups on the pharmaceutically active compound ranges from about 2:1 to 10:1. In one embodiment, the molar ratio of amine groups on the lysine-vitamin ester relative to acidic groups on the pharmaceutically active compound ranges from about 2:1 to 12:1.

In one embodiment, the molar ratio of amine groups on the lysine-vitamin ester relative to acidic groups on the pharmaceutically active compound is greater than about 1:1 and some or all of the excess amino groups on the amino acid ester or amide of lysine are neutralized with a carboxylic acid. In one embodiment, the molar ratio of amine groups on the lysine-vitamin ester relative to acidic groups on the pharmaceutically active compound is greater than about 1:1 and some or all of the excess amino groups on the amino acid ester or amide of lysine are neutralized with a fatty acid. Any of the fatty acids described above can be used to neutralize the excess amino groups on the lysine-vitamin ester.

6.7.2 Pharmaceutical Compositions Comprising (i) an Amino Acid-vitamin Ester, (ii) a Carboxylic Acid, and (iii) a Neutral Non-acidic Pharmaceutically Active Compound or a Pharmaceutically Acceptable Salt of a Pharmaceutically Active Compound The amino acid-vitamin ester can be any amino acid-vitamin ester described above.

The carboxylic acid can be any carboxylic acid described above.

In one embodiment, the carboxylic acid is a fatty acid.

In one embodiment, the carboxylic acid is an N-acyl amino acid.

In one embodiment, the pharmaceutical composition is a solid. Without wishing to be bound by theory, it is believed that the solid comprises a salt formed between the amino acid-vitamin ester and the carboxylic acid wherein the carboxylic acidic protonates the α-amino group of the amino acid-vitamin ester.

In one embodiment, the pharmaceutically active compound is a neutral non-acidic pharmaceutically active compound. In one embodiment, the pharmaceutically active compound is a pharmaceutically acceptable salt of a basic or acidic pharmaceutically active compound. In one embodiment, the pharmaceutically active compound is a pharmaceutically acceptable salt of an acidic pharmaceutically active compound. In one embodiment, the pharmaceutically active compound is a pharmaceutically acceptable salt of a basic pharmaceutically active compound.

When the pharmaceutically active compound is a neutral non-acidic pharmaceutically active compound, the pharmaceutical composition includes about 1 equivalent of amino acid-vitamin ester for each equivalent of acidic groups in the carboxylic acid. For example, if the carboxylic acid is a mono-protic carboxylic acid, the pharmaceutical composition includes about 1 equivalent of amino acid-vitamin ester for each equivalent of carboxylic acid and, if the carboxylic acid is a di-carboxylic acid, the pharmaceutical composition includes about 2 equivalent of amino acid-vitamin ester for each equivalent of carboxylic acid.

Similarly, when the pharmaceutically active compound is a salt of a pharmaceutically active compound, the pharmaceutical composition includes about 1 equivalent of amino acid-vitamin ester for each equivalent of acidic groups in the carboxylic acid.

In one embodiment, the pharmaceutically active compound is a neutral non-acidic pharmaceutically active compound and the carboxylic acid is a fatty acid.

In one embodiment, the pharmaceutically active compound is a neutral non-acidic pharmaceutically active compound and the carboxylic acid is an N-acyl amino acid.

In one embodiment, the pharmaceutically active compound is a pharmaceutically acceptable salt of an acidic or basic pharmaceutically active compound.

In one embodiment, the salt of the pharmaceutically active compound is a salt formed between a basic pharmaceutically active compound and an acid.

In one embodiment, the salt of the pharmaceutically active compound is a salt formed between a basic pharmaceutically active compound and a carboxylic acid.

In one embodiment, the salt of the pharmaceutically active compound is a salt formed between a basic pharmaceutically active compound and a fatty acid.

In one embodiment, the salt of the pharmaceutically active compound is a salt formed between a basic pharmaceutically active compound and an N-acyl amino acid.

In one embodiment, the salt of the pharmaceutically active compound is a salt formed between an acidic pharmaceutically active compound and a base.

In one embodiment, the salt of the pharmaceutically active compound is a salt formed between an acidic pharmaceutically active compound and an amino acid-vitamin ester.

In one embodiment, the carboxylic acid is a fatty acid and the pharmaceutically active compound is a pharmaceutically acceptable salt of an acidic or basic pharmaceutically active compound.

In one embodiment, the carboxylic acid is a fatty acid and the salt of the pharmaceutically active compound is a salt formed between a basic pharmaceutically active compound and an acid.

In one embodiment, the carboxylic acid is a fatty acid and the salt of the pharmaceutically active compound is a salt formed between a basic pharmaceutically active compound and a carboxylic acid.

In one embodiment, the carboxylic acid is a fatty acid and the salt of the pharmaceutically active compound is a salt formed between a basic pharmaceutically active compound and a fatty acid.

In one embodiment, the carboxylic acid is a fatty acid and the salt of the pharmaceutically active compound is a salt formed between a basic pharmaceutically active compound and an N-acyl amino acid.

In one embodiment, the carboxylic acid is a fatty acid and the salt of the pharmaceutically active compound is a salt formed between an acidic pharmaceutically active compound and a base.

In one embodiment, the carboxylic acid is a fatty acid and the salt of the pharmaceutically active compound is a salt formed between an acidic pharmaceutically active compound and an amino acid-vitamin ester.

In one embodiment, the carboxylic acid is an N-acyl amino acid and the pharmaceutically active compound is a pharmaceutically acceptable salt of an acidic or basic pharmaceutically active compound.

In one embodiment, the carboxylic acid is an N-acyl amino acid and the salt of the pharmaceutically active compound is a salt formed between a basic pharmaceutically active compound and an acid.

In one embodiment, the carboxylic acid is an N-acyl amino acid and the salt of the pharmaceutically active compound is a salt formed between a basic pharmaceutically active compound and a carboxylic acid.

In one embodiment, the carboxylic acid is an N-acyl amino acid and the salt of the pharmaceutically active compound is a salt formed between a basic pharmaceutically active compound and a fatty acid.

In one embodiment, the carboxylic acid is an N-acyl amino acid and the salt of the pharmaceutically active compound is a salt formed between a basic pharmaceutically active compound and an N-acyl amino acid.

In one embodiment, the carboxylic acid is an N-acyl amino acid and the salt of the pharmaceutically active compound is a salt formed between an acidic pharmaceutically active compound and a base.

In one embodiment, the carboxylic acid is an N-acyl amino acid and the salt of the pharmaceutically active compound is a salt formed between an acidic pharmaceutically active compound and an amino acid-vitamin ester.

The amount of the neutral non-acidic pharmaceutically active compound or pharmaceutically acceptable salt of a pharmaceutically active compound in the pharmaceutical compositions typically ranges from about 1 to 90 percent by weight of the pharmaceutical composition, preferably about 5 to 80 percent by weight of the pharmaceutical composition, more preferably about 7.5 to 70 percent by weight of the pharmaceutical composition, and most preferably about 10 to 60 by weight of the pharmaceutical composition.

The combined amount of the amino acid-vitamin ester and the carboxylic acid in the pharmaceutical compositions typically ranges from about 1 to 75 percent by weight of the pharmaceutical composition. In one embodiment, the combined amount of the amino acid-vitamin ester and the carboxylic acid in the pharmaceutical compositions ranges from about 2 to 50 percent by weight of the composition. In one embodiment, the combined amount of the amino acid-vitamin ester and the carboxylic acid in the pharmaceutical compositions ranges from about 2 percent to 25 percent by weight of the pharmaceutical composition. In one embodiment, the combined amount of the amino acid-vitamin ester and the carboxylic acid in the pharmaceutical compositions ranges from about 5 percent to 20 percent by weight of the pharmaceutical composition. In one embodiment, the combined amount of the amino acid-vitamin ester and the carboxylic acid in the pharmaceutical compositions ranges from about 5 percent to 15 percent by weight of the pharmaceutical composition.

The combined amount of the amino acid-vitamin ester, the carboxylic acid, and the neutral non-acidic pharmaceutically active compound or pharmaceutically acceptable salt of a pharmaceutically active compound in the pharmaceutical composition typically ranges from about 2 percent to 90 percent of the composition. In one embodiment, the combined amount of the amino acid-vitamin ester, the carboxylic acid, and the neutral non-acidic pharmaceutically active compound or pharmaceutically acceptable salt of a pharmaceutically active compound in the pharmaceutical composition ranges from about 2 percent to about 75 percent of the composition. In one embodiment, the combined amount of the amino acid-vitamin ester, the carboxylic acid, and the neutral non-acidic pharmaceutically active compound or pharmaceutically acceptable salt of a pharmaceutically active compound ranges from about 2 percent to about 60 percent of the composition. In one embodiment, the combined amount of the amino acid-vitamin ester, the carboxylic acid, and the neutral non-acidic pharmaceutically active compound or pharmaceutically acceptable salt of a pharmaceutically active compound in the pharmaceutical composition ranges from about 2 percent to about 50 percent of the composition. In one embodiment, the combined amount of the amino acid-vitamin ester, the carboxylic acid, and the neutral non-acidic pharmaceutically active compound or pharmaceutically acceptable salt of a pharmaceutically active compound in the pharmaceutical composition ranges from about 5 percent to about 50 percent of the composition. In one embodiment, the combined amount of the amino acid-vitamin ester, the carboxylic acid, and the neutral non-acidic pharmaceutically active compound or pharmaceutically acceptable salt of a pharmaceutically active compound in the pharmaceutical composition ranges from about 5 percent to about 35 percent of the composition. In one embodiment, the combined amount of the amino acid-vitamin ester, the carboxylic acid, and the neutral non-acidic pharmaceutically active compound or pharmaceutically acceptable salt of a pharmaceutically active compound in the pharmaceutical composition ranges from about 5 percent to about 25 percent of the composition. In one embodiment, the combined amount of the amino acid-vitamin ester, the carboxylic acid, and the neutral non-acidic pharmaceutically active compound or pharmaceutically acceptable salt of a pharmaceutically active compound in the pharmaceutical composition ranges from about 5 percent to about 20 percent of the composition. In one embodiment, the combined amount of the amino acid-vitamin ester, the carboxylic acid, and the neutral non-acidic pharmaceutically active compound or pharmaceutically acceptable salt of a pharmaceutically active compound in the pharmaceutical composition ranges from about 5 percent to about 15 percent of the composition.

One of ordinary skill in the art will recognize, however, that the combined amount of the amino acid-vitamin ester, the carboxylic acid, and the neutral non-acidic pharmaceutically active compound or pharmaceutically acceptable salt of a pharmaceutically active compound in the pharmaceutical composition can vary widely depending on the pharmaceutically active compound, the amino acid-vitamin ester, the carboxylic acid, the solvent and used in the pharmaceutical composition.

In one embodiment, the pharmaceutical composition further comprises a pharmaceutically acceptable organic solvent. The pharmaceutically acceptable organic solvent can be any pharmaceutically acceptable organic solvent described above.

In one embodiment, the pharmaceutical composition further comprising a pharmaceutically acceptable organic solvent is a suspension of solid particles in the pharmaceutically acceptable organic solvent. Without wishing to be bound by theory, it is believed that the solid particles are a salt formed between the amino acid-vitamin ester and the carboxylic acid wherein the carboxylic acid protonates the α-amino group of the amino acid-vitamin ester.

In one embodiment, comprising a pharmaceutically acceptable organic solvent, the pharmaceutical composition is injectable. In one embodiment, the pharmaceutical composition further comprising a pharmaceutically acceptable organic solvent is a solution. In one embodiment, comprising a pharmaceutically acceptable organic solvent, the pharmaceutical composition is injectable and forms a precipitate when injected into water.

Again, without wishing to be bound by theory, it is believed that when the pharmaceutical compositions further comprising a pharmaceutically acceptable organic solvent are injected into an animal, the pharmaceutically acceptable organic solvent diffuses away from the injection site and aqueous bodily fluids diffuse towards the injection site, resulting in an increase in concentration of water at the injection site, that causes at least a portion of the composition to precipitate and form a drug depot. Again, when the pharmaceutical composition is injected into an animal, the salt of the amino acid-vitamin ester and the carboxylic acid precipitates to form a drug depot that slowly releases the pharmaceutically active compound. The salt of the pharmaceutically active compound, however, may also form a precipitate.

In one embodiment, the pharmaceutical composition comprises the amino acid-vitamin ester, a fatty acid, a salt of a pharmaceutically active compound, and a pharmaceutically acceptable organic solvent, wherein the salt of the pharmaceutically active compound is a salt formed between an acidic pharmaceutically active compound and an amino acid-vitamin ester. In this embodiment, a salt formed between the amino acid-vitamin ester and the fatty acid precipitates and a salt formed between the acidic pharmaceutically active compound and the amino acid-vitamin ester precipitates when the pharmaceutical composition is injected into an animal to form a drug depot that slowly releases the pharmaceutically active compound over time.

In another embodiment, the pharmaceutical composition comprises the amino acid-vitamin ester, a N-acyl amino acid, a salt of a pharmaceutically active compound, and a pharmaceutically acceptable organic solvent, wherein the salt of the pharmaceutically active compound is a salt formed between an acidic pharmaceutically active compound and an amino acid-vitamin ester. In this embodiment, a salt formed between the amino acid-vitamin ester and the N-acyl amino acid precipitates and a salt formed between the acidic pharmaceutically active compound and the amino acid-vitamin ester precipitates when the pharmaceutical composition is injected into an animal to form a drug depot that slowly releases the pharmaceutically active compound over time.

When the compositions include an amino acid-vitamin ester, a carboxylic acid, and a salt of a pharmaceutically active compound, it is recognized that there will be an exchange of the anions (and cations) that form the salt of the pharmaceutically active compound with the anions (and cations) that form the salt between the carboxylic acid and the amino acid-vitamin ester. For example, if the salt of a pharmaceutically active compound is a salt formed between a basic pharmaceutically active compound and a fatty acid and the carboxylic acid is a N-acyl amino acid, the pharmaceutical composition will include each of the following species: a salt between the basic pharmaceutically active compound and the fatty acid, a salt between the basic pharmaceutically active compound and the N-acyl amino acid, a salt between the amino acid-vitamin ester and the fatty acid, and a salt between the amino acid-vitamin ester and the N-acyl amino acid. Any one or all of these species can precipitate when the pharmaceutical composition is injected into an animal to form a drug depot that slowly releases the pharmaceutically active compound over time.

By varying the lipophilicity and/or molecular weight of the amino acid-vitamin ester it is possible to vary the rate at which the pharmaceutically active compound is released from the drug depot. Generally, the more lipophilic the amino acid-vitamin ester, the more slowly drug is released. The lipophilicity and/or molecular weight of the amino acid-vitamin ester can be varied by varying the amino acid and/or the vitamin used to form the amino acid-vitamin ester. For example, the lipophilicity and/or molecular weight of the amino acid-vitamin ester can be varied by varying the R group of the amino acid or the vitamin. For example, when R is a hydrocarbon group, the higher the molecular weight of R, the more lipophilic is the amino acid-vitamin ester. The rate at which the pharmaceutically active compound is released from the drug depot can also be varied by varying the lipophilicity and/or molecular weight of the carboxylic acid. Generally, the more lipophilic the carboxylic acid, the more slowly drug is released. The lipophilicity and/or molecular weight of the carboxylic acid can be varied by varying the molecular weight of the carboxylic acid. Generally, the higher the molecular weight of the carboxylic acid, the more slowly drug is released.

In one embodiment, the pharmaceutically active compound is insulin.

In one embodiment, the pharmaceutically active compound is fluoxetine. Pharmaceutical compositions of the invention containing fluoxetine can be administered to dogs to treat separation anxiety and to cats to treat spraying.

In one embodiment, the pharmaceutically active compound is a fluoroquinolone. The fluoroquinolone can be any fluoroquinolone known to those skilled in the art. Representative fluoroquinolones useful in the compositions and methods of the invention include, but are not limited to, those described in BE 870,576, U.S. Pat. No. 4,448,962, DE 3,142,854, EP 047,005, EP 206,283, BE 887,574, EP 221,463, EP 140,116, EP 131,839, EP 154,780, EP 078,362, EP 310,849, EP 520,240, U.S. Pat. No. 4,499,091, U.S. Pat. No. 4,704,459, U.S. Pat. No. 4,795,751, U.S. Pat. No. 4,668,784, and U.S. Pat. No. 5,532,239, the contents of which are expressly incorporated herein by reference thereto.

Representative fluoroquinolones useful in the compositions and methods of the invention include, but are not limited to, ciprofloxacin (commercially available as Cipro®), enrofloxacin (commercially available as Baytril®), enoxacin (commercially available as Penetrex®), gatifloxacin (commercially available as Tequin®), gemifloxacin (commercially available as Factive®), levofloxacin (commercially available as Levaquin®), lomefloxacin (commercially available as Maxaquin®), moxifloxacin (commercially available as Avelox®), norfloxacin (commercially available as Noroxin®), ofloxacin (commercially available as Floxin®), sparfloxacin (commercially available as Zagam®), trovafloxacin (commercially available as Trovan®), difloxacin, cinofloxacin, pefloxacin, tosufloxacin, temafloxacin, flerofloxacin, amifloxacin, benofloxacin, danofloxacin, flerofloxacin, marbofloxacin, ruflocaxin, and sarafloxacin.

In one embodiment, the fluoroquinolone is ciprofloxacin.
In one embodiment, the fluoroquinolone is enrofloxacin.
In one embodiment, the fluoroquinolone is gatifloxacin.
In one embodiment, the fluoroquinolone is gemifloxacin.
In one embodiment, the fluoroquinolone is levofloxacin.
In one embodiment, the fluoroquinolone is lomefloxacin.
In one embodiment, the fluoroquinolone is moxifloxacin.
In one embodiment, the fluoroquinolone is ofloxacin.
In one embodiment, the fluoroquinolone is sparfloxacin.
In one embodiment, the fluoroquinolone is trovafloxacin.
In one embodiment, the fluoroquinolone is difloxacin.
In one embodiment, the fluoroquinolone is cinofloxacin.
In one embodiment, the fluoroquinolone is pefloxacin.
In one embodiment, the fluoroquinolone is tosufloxacin.
In one embodiment, the fluoroquinolone is temafloxacin.
In one embodiment, the fluoroquinolone is flerofloxacin.
In one embodiment, the fluoroquinolone is amifloxacin.
In one embodiment, the fluoroquinolone is benofloxacin.
In one embodiment, the fluoroquinolone is danofloxacin.
In one embodiment, the fluoroquinolone is flerofloxacin.
In one embodiment, the fluoroquinolone is marbofloxacin.
In one embodiment, the fluoroquinolone is ruflocaxin.
In one embodiment, the fluoroquinolone is sarafloxacin.

6.7.3 Pharmaceutical Compositions Comprising (i) an Amino Acid-vitamin Ester and (ii) a Protonated Oligonucleotide In one embodiment, the pharmaceutical composition comprises (i) an amino acid-vitamin ester and (ii) a protonated oligonucleotide, i.e., the pharmaceutically active compound is an oligonucleotide. Without wishing to be bound by theory, it is believed that the acidic phosphate groups of the protonated oligonucleotide protonate the amine group of the amino acid-vitamin ester to form a salt between one or more amino acid-vitamin ester molecules and the oligonucleotide as illustrated schematically below:

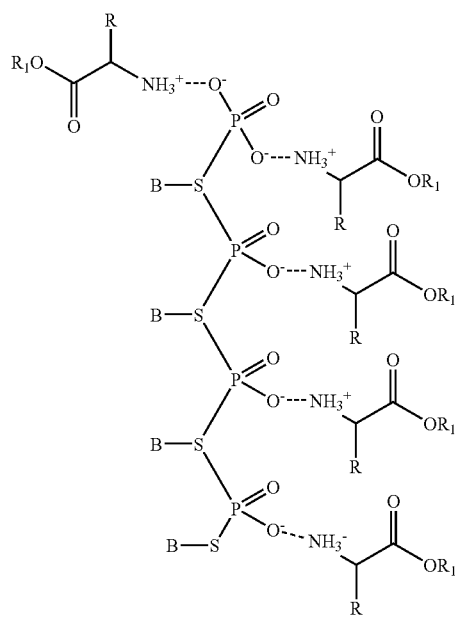

wherein B is a nucleotide, S is a sugar, R is amino acid side chain, and —OR$_1$ is the residue of a vitamin. It is not necessary, however, that every phosphate group be ionically bound to an amino acid-vitamin ester.

Any amino acid-vitamin ester described above can be used in the pharmaceutical compositions.

Any oligonucleotide described above can be used in the pharmaceutical compositions.

The molar ratio of acidic groups on the oligonucleotide to basic groups on the amino acid-vitamin ester typically ranges from about 2:1 to 1:2. In one embodiment, the molar ratio of acidic groups on the oligonucleotide to basic groups on the amino acid-vitamin ester ranges from about 1.5:1 to 1:1.5. In one embodiment, the molar ratio of acidic groups on the oligonucleotide to basic groups on the amino acid-vitamin ester ranges from about 1.25:1 to 1:1.25. In one embodiment, the molar ratio of acidic groups on the oligonucleotide to basic groups on the amino acid-vitamin ester ranges from about 1.1:1. to 1:1.1. In one embodiment, the molar ratio of acidic groups on the oligonucleotide to basic groups on the amino acid-vitamin ester is about 1:1. A wider range for the molar ratio of acidic groups on the oligonucleotide to basic groups on the amino acid-vitamin ester, however, is also possible. For example, the molar ratio of acidic groups on the oligonucleotide to basic groups on the amino acid-vitamin ester can range from about 15:1 to 1:15.

In one embodiment, the pharmaceutical composition further comprises a pharmaceutically acceptable organic solvent. Any pharmaceutically acceptable organic solvent can be used in the pharmaceutical compositions of the invention. Representative, pharmaceutically acceptable organic solvents include, but are not limited to, pyrrolidone, N-methyl-2-pyrrolidone, polyethylene glycol, propylene glycol (i.e., 1,3-propylene glycol), glycerol formal, isosorbide dimethyl ether, ethanol, dimethyl sulfoxide, tetraglycol, tetrahydrofurfuryl alcohol, triacetin, propylene carbonate, dimethyl acetamide, dimethyl formamide, dimethyl sulfoxide, and combinations thereof.

Typically, oligonucleotides are available as the salt of a metal cation, for example, as the potassium or sodium salt. These salts, however, have low solubility in organic solvents, typically, less than about 25 mg/mL. The pharmaceutical compositions of the invention comprising (i) an amino acid-vitamin ester and (ii) a protonated oligonucleotide, however, are significantly more soluble in organic solvents. Without wishing to be bound by theory, it is believed that the amino acid-vitamin ester and the protonated oligonucleotide form a salt, such as illustrated above, and the salt is soluble organic solvents.

The combined amount of the oligonucleotide and amino acid-vitamin ester in pharmaceutical compositions that further comprise a pharmaceutically acceptable organic solvent typically ranges from about 1 to 90 percent by weight of the pharmaceutical composition, preferably about 5 to 80 percent by weight of the pharmaceutical composition, more preferably about 7.5 to 70 percent by weight of the pharmaceutical composition, and most preferably about 10 to 60 by weight of the pharmaceutical composition.

One of ordinary skill in the art will recognize, however, that the amount of the oligonucleotide and amino acid-vitamin ester in the pharmaceutical composition can vary widely depending on the oligonucleotide, the amino acid-vitamin ester, and the solvent used in the pharmaceutical composition.

In one embodiment, comprising a pharmaceutically acceptable organic solvent, the pharmaceutical composition is injectable. In one embodiment, the pharmaceutical composition further comprising a pharmaceutically acceptable organic solvent is a solution. In one embodiment, comprising a pharmaceutically acceptable organic solvent, the pharmaceutical composition is injectable and forms a precipitate when injected into water.

Again, without wishing to be bound by theory, it is believed that when the pharmaceutical compositions further comprising a pharmaceutically acceptable organic solvent are injected into an animal, the pharmaceutically acceptable organic solvent diffuses away from the injection site and aqueous bodily fluids diffuse towards the injection site, resulting in an increase in concentration of water at the injection site, that causes at least a portion of the composition to precipitate and form a drug depot. Again, when the pharmaceutical composition is injected into an animal, the salt of the amino acid-vitamin ester and the oligonucleotide precipitates to form a drug depot that slowly releases the oligonucleotide.

In one embodiment, the concentration of the oligonucleotide in the pharmaceutically acceptable organic solvent is greater than about 2 percent by weight of the pharmaceutical composition. In one embodiment, the concentration of the oligonucleotide in the pharmaceutically acceptable organic solvent is greater than about 5 percent by weight of the pharmaceutical composition. In one embodiment, the concentration of the oligonucleotide in the pharmaceutically acceptable organic solvent is greater than about 7.5 percent by weight of the pharmaceutical composition. In one embodiment, the concentration of the oligonucleotide in the pharmaceutically acceptable organic solvent is greater than about 10 percent by weight of the pharmaceutical composition. In one embodiment, the concentration of the oligonucleotide in the pharmaceutically acceptable organic solvent is greater than about 12 percent by weight of the pharmaceutical composition. In one embodiment, the concentration of the oligonucleotide in the pharmaceutically acceptable organic solvent is greater than about 15 percent by weight of the pharmaceutical composition. In one embodiment, the concentration of the oligonucleotide in the pharmaceutically acceptable organic solvent is ranges from about 2 percent to 5 percent by weight of the pharmaceutical composition. In one embodiment, the concentration of the oligonucleotide in the pharmaceutically acceptable organic solvent is ranges from about 2 percent to 7.5 percent by weight of the pharmaceutical composition. In one embodiment, the concentration of the oligonucleotide in the pharmaceutically acceptable organic solvent ranges from about 2 percent to 10 percent by weight of the pharmaceutical composition. In one embodiment, the concentration of the oligonucleotide in the pharmaceutically acceptable organic solvent is ranges from about 2 percent to 12 percent by weight of the pharmaceutical composition. In one embodiment, the concentration of the oligonucleotide in the pharmaceutically acceptable organic solvent is ranges from about 2 percent to 15 percent by weight of the pharmaceutical composition. In one embodiment, the concentration of the oligonucleotide in the pharmaceutically acceptable organic solvent is ranges from about 2 percent to 20 percent by weight of the pharmaceutical composition.

In one embodiment, the pharmaceutically acceptable organic solvent is a water soluble solvent. A representative pharmaceutically acceptable water soluble organic solvent is triacetin.

In one embodiment, the pharmaceutically acceptable organic solvent is a water miscible solvent. Representative pharmaceutically acceptable water miscible organic solvents include, but are not limited to, glycerol formal, polyethylene glycol, and propylene glycol.

In one embodiment, the pharmaceutically acceptable organic solvent comprises pyrrolidone. In one embodiment, the pharmaceutically acceptable organic solvent is pyrrolidone substantially free of another organic solvent.

In one embodiment, the pharmaceutically acceptable organic solvent comprises N-methyl-2-pyrrolidone. In one embodiment, the pharmaceutically acceptable organic solvent is N-methyl-2-pyrrolidone substantially free of another organic solvent.

In one embodiment, the pharmaceutically acceptable organic solvent comprises polyethylene glycol. In one embodiment, the pharmaceutically acceptable organic solvent is polyethylene glycol substantially free of another organic solvent.

In one embodiment, the pharmaceutically acceptable organic solvent comprises propylene glycol. In one embodiment, the pharmaceutically acceptable organic solvent is propylene glycol substantially free of another organic solvent.

In one embodiment, the pharmaceutically acceptable organic solvent comprises glycerol formal. In one embodiment, the pharmaceutically acceptable organic solvent is glycerol formal substantially free of another organic solvent.

In one embodiment, the pharmaceutically acceptable organic solvent comprises isosorbid dimethyl ether. In one embodiment, the pharmaceutically acceptable organic solvent is isosorbid dimethyl ether substantially free of another organic solvent.

In one embodiment, the pharmaceutically acceptable organic solvent comprises ethanol. In one embodiment, the pharmaceutically acceptable organic solvent is ethanol substantially free of another organic solvent.

In one embodiment, the pharmaceutically acceptable organic solvent comprises dimethyl sulfoxide. In one embodiment, the pharmaceutically acceptable organic solvent is dimethyl sulfoxide substantially free of another organic solvent.

In one embodiment, the pharmaceutically acceptable organic solvent comprises tetraglycol. In one embodiment, the pharmaceutically acceptable organic solvent is tetraglycol substantially free of another organic solvent.

In one embodiment, the pharmaceutically acceptable organic solvent comprises tetrahydrofurfuryl alcohol. In one embodiment, the pharmaceutically acceptable organic solvent is tetrahydrofurfuryl alcohol substantially free of another organic solvent.

In one embodiment, the pharmaceutically acceptable organic solvent comprises triacetin. In one embodiment, the pharmaceutically acceptable organic solvent is triacetin substantially free of another organic solvent.

In one embodiment, the pharmaceutically acceptable organic solvent comprises propylene carbonate. In one embodiment, the pharmaceutically acceptable organic solvent is propylene carbonate substantially free of another organic solvent.

In one embodiment, the pharmaceutically acceptable organic solvent comprises dimethyl acetamide. In one embodiment, the pharmaceutically acceptable organic solvent is dimethyl acetamide substantially free of another organic solvent.

In one embodiment, the pharmaceutically acceptable organic solvent comprises dimethyl formamide. In one embodiment, the pharmaceutically acceptable organic solvent is dimethyl formamide substantially free of another organic solvent.

In one embodiment, the pharmaceutically acceptable organic solvent comprises at least two pharmaceutically acceptable organic solvents.

In one embodiment, the pharmaceutically acceptable organic solvent comprises N-methyl-2-pyrrolidone and glycerol formal. In one embodiment, the pharmaceutically acceptable organic solvent is N-methyl-2-pyrrolidone and glycerol formal. In one embodiment, the ratio of N-methyl-2-pyrrolidone to glycerol formal ranges from about 90:10 to 10:90.

In one embodiment, the pharmaceutically acceptable organic solvent comprises propylene glycol and glycerol formal. In one embodiment, the pharmaceutically acceptable organic solvent is propylene glycol and glycerol formal. In one embodiment, the ratio of propylene glycol to glycerol formal ranges from about 90:10 to 10:90.

In one embodiment, the pharmaceutically acceptable organic solvent is a solvent that is recognized as GRAS by the FDA for administration or consumption by animals.

In one embodiment, the pharmaceutically acceptable organic solvent is a solvent that is recognized as GRAS by the FDA for administration or consumption by humans.

In one embodiment, the pharmaceutically acceptable organic solvent is substantially free of water. In one embodiment, the pharmaceutically acceptable organic solvent contains less than about 1 percent by weight of water. In one embodiment, the pharmaceutically acceptable organic solvent contains less about 0.5 percent by weight of water. In one embodiment, the pharmaceutically acceptable organic solvent contains less about 0.2 percent by weight of water. Pharmaceutically acceptable organic solvents that are substantially free of water are advantageous since they are not conducive to bacterial growth. Accordingly, it is typically not necessary to include a preservative in pharmaceutical compositions that are substantially free of water. Another advantage of pharmaceutical compositions that use a pharmaceutically acceptable organic solvent, preferably substantially free of water, as the solvent is that hydrolysis of the oligonucleotide is minimized. Typically, the more water present in the solvent the more readily the oligonucleotide can be hydrolyzed. Accordingly, oligonucleotide containing pharmaceutical compositions that use a pharmaceutically acceptable organic solvent as the solvent can be more stable than oligonucleotide containing pharmaceutical compositions that use water as the solvent.

In one embodiment, comprising a pharmaceutically acceptable organic solvent, the pharmaceutical composition is injectable.

In one embodiment, the injectable pharmaceutical compositions are of sufficiently low viscosity that they can be easily drawn into a 20 gauge and needle and then easily expelled from the 20 gauge needle. Typically, the viscosity of the injectable pharmaceutical compositions are less than about 1,200 cps. In one embodiment, the viscosity of the injectable pharmaceutical compositions are less than about 1,000 cps. In one embodiment, the viscosity of the injectable pharmaceutical compositions are less than about 800 cps. In one embodiment, the viscosity of the injectable pharmaceutical compositions are less than about 500 cps. Injectable pharmaceutical compositions having a viscosity greater than about 1,200 cps and even greater than about 2,000 cps (for example gels) are also within the scope of the invention provided that the compositions can be expelled through an 18 to 24 gauge needle.

In one embodiment, comprising a pharmaceutically acceptable organic solvent, the pharmaceutical composition is injectable and does not form a precipitate when injected into water.

In one embodiment, comprising a pharmaceutically acceptable organic solvent, the pharmaceutical composition is injectable and forms a precipitate when injected into water. Without wishing to be bound by theory, it is believed, for pharmaceutical compositions that comprise a protonated oligonucleotide and an amino acid-vitamin ester, that the α-amino group of the amino acid-vitamin ester is protonated by the oligonucleotide to form a salt, such as illustrated above, which is soluble in the pharmaceutically acceptable organic solvent but insoluble in water. Accordingly, when the pharmaceutical compositions are injected into an animal, at least a portion of the pharmaceutical composition precipitates at the injection site to provide a drug depot. Without wishing to be bound by theory, it is believed that when the pharmaceutically compositions are injected into an animal, the pharmaceutically acceptable organic solvent diffuses away from the injection site and aqueous bodily fluids diffuse towards the injection site, resulting in an increase in concentration of water at the injection site, that causes at least a portion of the composition to precipitate and form a drug depot. The precipitate can take the form of a solid, a crystal, a gummy mass, or a gel. The precipitate, however, provides a depot of the oligonucleotide at the injection site that releases the oligonucleotide over time. The components of the pharmaceutical composition, i.e., the amino acid-vitamin ester, the pharmaceutically acceptable organic solvent, and any other components are biocompatible and non-toxic and, over time, are simply absorbed and/or metabolized by the body.

Release rates from a precipitate can be measured injecting about 50 µL of the pharmaceutical composition into about 4 mL of deionized water in a centrifuge tube. The time that the pharmaceutical composition is injected into the water is recorded as T=0. After a specified amount of time, T, the sample is cooled to about −9° C. and spun on a centrifuge at about 13,000 rpm for about 20 min. The resulting supernatant is then analyzed by HPLC to determine the amount of oligonucleotide present in the aqueous solution. The amount of oligonucleotide in the pellet resulting from the centrifugation can also be determined by collecting the pellet, dissolving the pellet in about 10 µL of methanol, and analyzing the methanol solution by HPLC to determine the amount of oligonucleotide in the precipitate. The amount of oligonucleotide in the aqueous solution and the amount of oligonucleotide in the precipitate are determined by comparing the peak area for the HPLC peak corresponding to the oligonucleotide against a standard curve of oligonucleotide peak area against concentration of oligonucleotide. Suitable HPLC conditions can be readily determined by one of ordinary skill in the art.

In one embodiment, comprising a pharmaceutically acceptable organic solvent, the pharmaceutical composition is injectable and forms liposomal or micellar structures when injected into water (typically about 500 µL are injected into about 4 mL of water). The formation of liposomal or micellar structures are most often formed when the pharmaceutical composition includes a phospholipid. Without wishing to be bound by theory, it is believed that the oligonucleotide in the form of a salt with an amino acid-vitamin ester is trapped within the liposomal or micellar structure. Without wishing to be bound by theory, it is believed that when these pharmaceutically compositions are injected into an animal, the liposomal or micellar structures release the oligonucleotide over time.

In one embodiment, the pharmaceutical composition further comprising a pharmaceutically acceptable organic solvent is a suspension of solid particles in the pharmaceutically acceptable organic solvent. Without wishing to be bound by theory, it is believed that the solid particles comprise a salt formed between the amino acid-vitamin ester and the protonated oligonucleotide wherein the acidic phosphate groups of the oligonucleotide protonates the amino group of the amino acid-vitamin ester, such as illustrated above. Pharmaceutical compositions that are suspensions can also form drug depots when injected into an animal.

In one embodiment, the pharmaceutical composition is a solution of the salt in the pharmaceutically acceptable organic solvent.

In one embodiment, the pharmaceutical composition comprises a pharmaceutically acceptable organic solvent and further comprises a phospholipid, a sphingomyelin, or phosphatidyl choline. Without wishing to be bound by theory, it is believed that the phospholipid, sphingomyelin, or phosphatidyl choline facilitates formation of a precipitate when the pharmaceutical composition is injected into water and can also facilitate controlled release of the oligonucleotide from the resulting precipitate. Typically, the phospholipid, sphingomyelin, or phosphatidyl choline is present in an amount ranging from greater than 0 to 10 percent by weight of the pharmaceutical composition. In one embodiment, the phospholipid, sphingomyelin, or phosphatidyl choline is present in an amount ranging from about 0.1 to 10 percent by weight of the pharmaceutical composition. In one embodiment, the phospholipid, sphingomyelin, or phosphatidyl choline is present in an amount ranging from about 1 to 7.5 percent by weight of the pharmaceutical composition. In one embodiment, the phospholipid, sphingomyelin, or phosphatidyl choline is present in an amount ranging from about 1.5 to 5 percent by weight of the pharmaceutical composition. In one embodiment, the phospholipid, sphingomyelin, or phosphatidyl choline is present in an amount ranging from about 2 to 4 percent by weight of the pharmaceutical composition.

In another embodiment, the pharmaceutical composition further comprises water as the solvent. In one embodiment, the pharmaceutical composition further comprising water is a suspension of solid particles in the water. Without wishing to be bound by theory, it is believed that the solid particles are a salt formed between the amino acid-vitamin ester and the oligonucleotide wherein the oligonucleotide protonates the α-amino group of the amino acid-vitamin ester. In one embodiment, the pharmaceutical composition further comprising water is injectable. In one embodiment, the pharmaceutical composition further comprising water is a solution.

6.7.3.i Pharmaceutical Compositions Wherein the Amino Acid-Vitamin Ester is an Amino Acid Ester of Lysine In one embodiment, the pharmaceutical composition comprises an amino acid-vitamin ester of lysine.

In one embodiment, there is less than a molar equivalent of lysine molecules relative to acidic phosphate groups on the oligonucleotide, i.e., there is an excess of acidic phosphate groups on the oligonucleotide relative to amino acid ester or amide molecules.

Without wishing to be bound by theory it is believed that the amino acid-vitamin ester of lysine cross-links two protonated oligonucleotide molecules as depicted below:

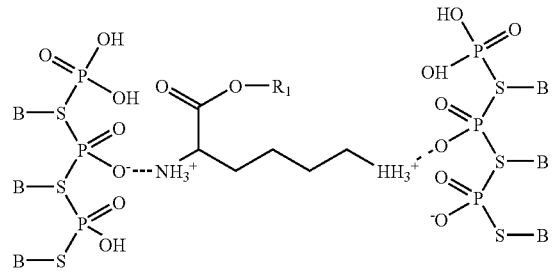

wherein B, S, and $R_1$ have the meaning described above.

Pharmaceutical Compositions Comprising an Amino-acid-vitamin Ester of Lysine, a Protonated Oligonucleotide, and a Carboxylic Acid In one embodiment, the amino acid-vitamin ester is an ester of lysine and the pharmaceutical composition further comprises a carboxylic acid. Without wishing to be bound by theory, it is believed that the carboxylic acid protonates the 1-amine group of lysine to provide a structure as depicted below:

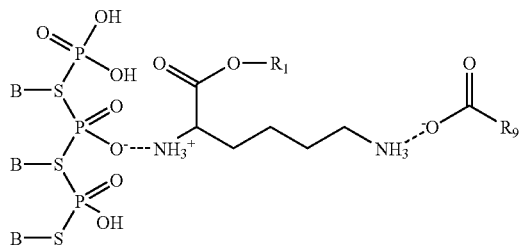

wherein B, S, and $R_1$ are defined above and $R_9$ is a $C_1$-$C_{21}$ hydrocarbon.

The combined molar ratio of acidic groups on the oligonucleotide and acid groups on the carboxylic acid to basic groups on the amino acid-vitamin ester typically ranges from about 2:1 to 1:2. In one embodiment, the combined molar ratio of acidic groups on the oligonucleotide and acid groups on the carboxylic acid to basic groups on the amino acid-vitamin ester ranges from about 1.5:1 to 1:1.5. In one embodiment, the combined molar ratio of acidic groups on the oligonucleotide and acid groups on the carboxylic acid to basic groups on the amino acid-vitamin ester ranges from about 1.25:1 to 1:1.25. In one embodiment, the combined molar ratio of acidic groups on the oligonucleotide and acid groups on the carboxylic acid to basic groups on the amino acid-vitamin ester ranges from about 1.1:1. to 1:1.1. In one embodiment, the combined molar ratio of acidic groups on the oligonucleotide and acid groups on the carboxylic acid to basic groups on the amino acid-vitamin ester is about 1:1. A wider range for the molar ratio of acidic groups on the oligonucleotide and acid groups on the carboxylic acid to basic groups on the amino acid-vitamin ester, however, is also possible. For example, the molar ratio of acidic groups on the oligonucleotide and acid groups on the carboxylic acid to basic groups on the amino acid-vitamin ester can range from about 15:1 to 1:15.

Generally, the molar ratio of acidic groups on the oligonucleotide to acid groups on the carboxylic acid ranges from about 20:1 to 1:20. In one embodiment, the molar ratio of acidic groups on the oligonucleotide to acid groups on the carboxylic acid ranges from about 15:1 to 1:15. In one embodiment, the molar ratio of acidic groups on the oligonucleotide to acid groups on the carboxylic acid ranges from about 10:1 to 1:10. In one embodiment, the molar ratio of acidic groups on the oligonucleotide to acid groups on the carboxylic acid ranges from about 5:1 to 1:5. In one embodiment, the molar ratio of acidic groups on the oligonucleotide to acid groups on the carboxylic acid ranges from about 2:1 to 1:2.

The Carboxylic Acid

The carboxylic acid can be any pharmaceutically acceptable carboxylic acid. Typically, the carboxylic acid is a $C_1$-$C_{22}$ carboxylic acid. Suitable carboxylic acids include, but are not limited to, acetic acid, propanoic acid, butanoic acid, pentanoic acid, decanoic acid, hexanoic acid, benzoic acid, caproic acid, lauric acid, myristic acid, palmitic acid, stearic acid, palmic acid, oleic acid, linoleic acid, and linolenic acid.

In one embodiment, the carboxylic acid is a $C_1$-$C_{16}$ carboxylic acid.

In one embodiment, the carboxylic acid is a $C_1$-$C_{10}$ carboxylic acid.

In one embodiment, the carboxylic acid is a $C_1$-$C_5$ carboxylic acid.

In one embodiment, the carboxylic acid is a $C_1$-$C_3$ carboxylic acid.

In one embodiment, the carboxylic acid is a $C_6$-$C_{22}$ carboxylic acid.

In one embodiment, the carboxylic acid is a $C_6$-$C_{18}$ carboxylic acid.

In one embodiment, the carboxylic acid is a $C_8$-$C_{18}$ carboxylic acid.

In one embodiment, the carboxylic acid is a $C_{10}$-$C_{18}$ carboxylic acid.

In one embodiment, the carboxylic acid is a $C_6$-$C_{18}$ carboxylic acid.

In one embodiment, the carboxylic acid is a $C_{16}$-$C_{22}$ carboxylic acid.

In one embodiment, the carboxylic acid is a saturated or unsaturated fatty acid.

In one embodiment, the carboxylic acid is a saturated fatty acid.

In one embodiment, the carboxylic acid is an unsaturated fatty acid.

In one embodiment, the carboxylic acid is a dicarboxylic acid. Suitable dicarboxylic acids include, but are not limited to, oxalic acid, malonic aid, succinic acid, glutamic acid, adipic acid, and pimelic acid.

In one embodiment, the carboxylic acid is a polycarboxylic acid.

The carboxylic acids are commercially available or can be prepared by methods well known to those skilled in the art.

In one embodiment, the carboxylic acid is an N-acyl amino acid. The N-acyl amino acids have the following general formula (III):

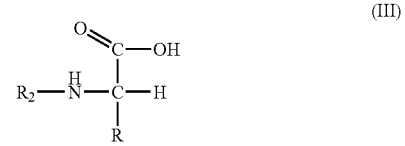

wherein:

R is the amino acid side chain and is defined above; and $R_2$ is an acyl group of formula —C(O)—$R_5$, wherein $R_5$ is a substituted $C_1$ to $C_{21}$ hydrocarbon group, i.e., the acyl group, $R_2$, is a $C_1$- to $C_{22}$ acyl group. Representative acyl groups of formula —C(O)—$R_5$ include, but are not limited to, acetyl, propionyl, butanoyl, hexanoyl, caproyl, heptoyl, octoyl, nonoyl, decoyl, undecoyl, dodecoyl, tridecoyl, tetradecoyl, pentadecoyl, hexadecoyl, heptadecoyl, octadecoyl, laurolyl, myristoyl, palmitoyl, stearoyl, palmioleoyl, oleoyl, linoleoyl, linolenoyl, and benzoyl.

In one embodiment, $R_5$ is a $C_1$-$C_{15}$ hydrocarbon group, i.e., the acyl group of formula —C(O)—$R_5$ is a $C_2$-$C_{16}$ acyl group.

In one embodiment, $R_5$ is a $C_1$-$C_9$ hydrocarbon group, i.e., the acyl group of formula —C(O)—$R_5$ is a $C_2$-$C_{10}$ acyl group.

In one embodiment, $R_5$ is a $C_1$-$C_5$ hydrocarbon group, i.e., the acyl group of formula —C(O)—$R_5$ is a $C_2$-$C_6$ acyl group.

In one embodiment, $R_5$ is a $C_1$-$C_3$ hydrocarbon group, i.e., the acyl group of formula —C(O)—$R_5$ is a $C_2$-$C_4$ acyl group.

In one embodiment, $R_5$ is a $C_5$-$C_2$, hydrocarbon group, i.e., the acyl group of formula —C(O)—$R_5$ is a $C_6$-$C_{22}$ acyl group.

In one embodiment, $R_5$ is a $C_5$-$C_{17}$ hydrocarbon group, i.e., the acyl group of formula —C(O)—$R_5$ is a $C_6$-$C_{18}$ acyl group.

In one embodiment, $R_5$ is a $C_7$-$C_{17}$ hydrocarbon group, i.e., the acyl group of formula —C(O)—$R_5$ is a $C_8$-$C_{18}$ acyl group.

In one embodiment, $R_5$ is a $C_9$-$C_{17}$ hydrocarbon group, i.e., the acyl group of formula —C(O)—$R_5$ is a $C_{10}$-$C_{18}$ acyl group.

In one embodiment, $R_5$ is a $C_{15}$-$C_{21}$ hydrocarbon group, i.e., the acyl group of formula —C(O)—$R_5$ is a $C_{16}$-$C_{22}$ acyl group.

In one embodiment, the acyl group of formula —C(O)—$R_5$ is obtained from a saturated or unsaturated fatty acid.

In one embodiment, the acyl group of formula —C(O)—$R_5$ is a caproyl, laurolyl, myristoyl, palmitoyl, stearoyl, palmioleoyl, oleoyl, linoleoyl, or linolenoyl group.

The N-acylated amino acids can be obtained by methods well known to those skilled in the art. For example, the N-acylated amino acids can be obtained by reacting an amino acid with an acid halide of formula T-C(O)—$R_5$, wherein T is a halide, preferably chloride, and $R_1$ is as defined above, using methods well known to those skilled in the art. When N-acylating the amino acid with the acid halide of formula T-C(O)—$R_5$, it may be necessary to protect some other functional group of the amino acid or the acid halide with a protecting group that is subsequently removed after the acylation reaction. One of ordinary skill in the art would readily know what functional groups would need to be protected before acylating the amino acid with the acid halide of formula T-C(O)—$R_5$. Suitable protecting groups are known to those skilled in the art such as those described in T. W. Greene, et al. *Protective Groups in Organic Synthesis,* 3 ed. (1999).

Acid halides can be obtained using methods well known to those skilled in the art such as those described in J. March, *Advanced Organic Chemistry, Reaction Mechanisms and Structure,* $4^{th}$ ed. John Wiley & Sons, NY, 1992, pp. 437-8. For example, acid halides can be prepared by reacting a carboxylic acid with thionyl chloride, bromide, or iodide. Acid chlorides and bromides can also be prepared by reacting a carboxylic acid with phosphorous trichloride or phosphorous tribromide, respectively. Acid chlorides can also be prepared by reacting a carboxylic acid with $Ph_3P$ in carbon tetrachloride. Acid fluorides can be prepared by reacting a carboxylic acid with cyanuric fluoride.

As discussed later, by varying the structure of carboxylic acid it is possible to vary the properties of the pharmaceutical compositions.

Pharmaceutical Compositions Comprising an Amino Acid-vitamin Ester of Lysine, a Protonated Aptamer, and a Phospholipid, Phosphatidyl Choline, or a Sphingomyelin In another embodiment, the amino acid-vitamin ester is an ester of lysine and the pharmaceutical composition further comprises a phospholipid, phosphatidyl choline, or a sphingomyelin. Without wishing to be bound by theory, it is believed that protonated phosphate groups on the phospholipid, phosphatidyl choline, or sphingomyelin protonates the ε-amine group of lysine to provide a structure as depicted below for a phospholipid:

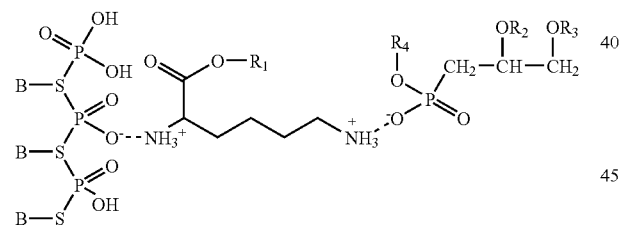

wherein B, S, $R_1$, $R_2$, $R_3$, and $R_4$ are defined above.

The combined molar ratio of acidic groups on the oligonucleotide and acidic groups on the phospholipid, phosphatidyl choline, or sphingomyelin to basic groups on the amino acid-vitamin ester typically ranges from about 2:1 to 1:2. In one embodiment, the combined molar ratio of acidic groups on the oligonucleotide and acidic groups on the phospholipid, phosphatidyl choline, or sphingomyelin to basic groups on the amino acid-vitamin ester ranges from about 1.5:1 to 1:1.5. In one embodiment, the combined molar ratio of acidic groups on the oligonucleotide and acidic groups on the phospholipid, phosphatidyl choline, or sphingomyelin to basic groups on the amino acid-vitamin ester ranges from about 1.25:1 to 1:1.25. In one embodiment, the combined molar ratio of acidic groups on the oligonucleotide and acidic groups on the phospholipid, phosphatidyl choline, or sphingomyelin to basic groups on the amino acid-vitamin ester ranges from about 1.1:1. to 1:1.1. In one embodiment, the combined molar ratio of acidic groups on the oligonucleotide and acidic groups on the phospholipid, phosphatidyl choline, or sphingomyelin to basic groups on the amino acid-vitamin ester is about 1:1. A wider range for the molar ratio of acidic groups on the oligonucleotide and acidic groups on the phospholipid, phosphatidyl choline, or sphingomyelin to basic groups on the amino acid-vitamin ester, however, is also possible. For example, the molar ratio of acidic groups on the oligonucleotide and acidic groups on the phospholipid, phosphatidyl choline, or sphingomyelin to basic groups on the amino acid-vitamin ester can range from about 15:1 to 1:15.

Generally, the molar ratio of acidic groups on the oligonucleotide to acidic groups on the phospholipid, phosphatidyl choline, or sphingomyelin ranges from about 20:1 to 1:20. In one embodiment, the molar ratio of acidic groups on the oligonucleotide to acidic groups on the phospholipid, phosphatidyl choline, or sphingomyelin ranges from about 15:1 to 1:15. In one embodiment, the molar ratio of acidic groups on the oligonucleotide to acidic groups on the phospholipid, phosphatidyl choline, or sphingomyelin ranges from about 10:1 to 1:10. In one embodiment, the molar ratio of acidic groups on the oligonucleotide to acidic groups on the phospholipid, phosphatidyl choline, or sphingomyelin ranges from about 5:1 to 1:5. In one embodiment, the molar ratio of acidic groups on the oligonucleotide to acidic groups on the phospholipid, phosphatidyl choline, or sphingomyelin ranges from about 2:1 to 1:2.

By varying the structure of phospholipid, phosphatidyl choline, or sphingomyelin it is possible to vary the properties of the pharmaceutical compositions.

The Phospholipid

Any pharmaceutically acceptable phospholipid can be used in the pharmaceutical compositions of the invention.

Representative, pharmaceutically acceptable phospholipids include, but are not limited to:

phosphatidic acids of general formula:

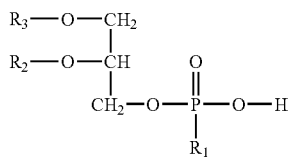

wherein $R_1$, $R_2$, and $R_3$ are defined above. Suitable phosphatidic acids suitable for use in the compositions and methods of the invention include, but are not limited to, the 1-acyl-2-acyl-sn-glycero-3-phosphates and the 1,2-diacyl-sn-glycero-3-phosphates commercially available from Avanti Polar Lipids Inc. of Alabaster, Ala.

phosphatidylethanolamines of general formula

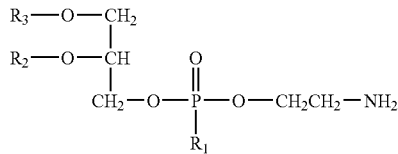

wherein $R_1$, $R_2$, and $R_3$ are defined above. Suitable phosphatidylethanolamines suitable for use in the compositions and methods of the invention include, but are not limited to, the 1-acyl-2-acyl-sn-glycero-3-phosphoethanolamines and the 1,2-diacyl-sn-glycero-3-phosphoethanolamines commercially available from Avanti Polar Lipids Inc. of Alabaster, Ala.

phosphatidylcholines of general formula

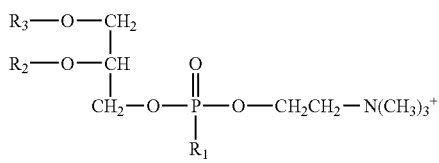

wherein $R_1$, $R_2$, and $R_3$ are defined above. Suitable phosphatidylcholines suitable for use in the compositions and methods of the invention include, but are not limited to, the 1-acyl-2-acyl-sn-glycero-3-phosphocholines, the 1,2-diacyl-sn-glycero-3-phosphoethanolamines (saturated series), and the 1,2-diacyl-sn-glycero-3-phosphoethanolamines (unsaturated series), commercially available from Avanti Polar Lipids Inc. of Alabaster, Ala. and Phospholipon®-50PG, Phospholipon®-53MCT, Phospholipon®-75SA, Phospholipon®-80, Phospholipon®-90NG, Phospholipon®-90H, and Phospholipon®-100H, commercially available from Phospholipid GmbH of Cologne, Germany. In one embodiment, the phospholipid is Phospholipon®-90H.

phosphatidylserines of general formula

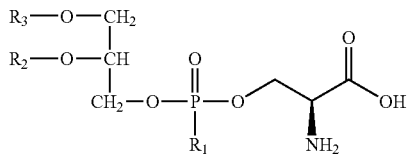

wherein $R_1$, $R_2$, and $R_3$ are defined above. Suitable phosphatidylserines suitable for use in the compositions and methods of the invention include, but are not limited to, the 1-acyl-2-acyl-sn-glycero-3-[phospho-L-serine]s and the 1,2-diacyl-sn-glycero-3-[phospho-L-serine]s commercially available from Avanti Polar Lipids Inc. of Alabaster, Ala.

plasmalogens of general formula

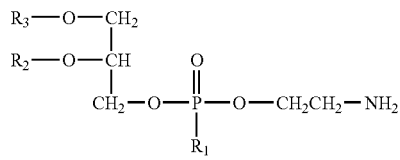

wherein $R_1$ and $R_2$ are defined above and $R_3$ is —C≡C—$R_9$, wherein $R_9$ is defined above. Suitable plasmalogens suitable for use in the compositions and methods of the invention include, but are not limited to, C16(Plasm)-12:0 NBD PC, C16(Plasm)-18:1 PC, C16(Plasm)-20:4 PC, C16(Plasm)-22:6 PC, C16(Plasm)-18:1 PC, C16(Plasm)-20:4 PE, and C16(Plasm)-22:6 PE, commercially available from Avanti Polar Lipids Inc. of Alabaster, Ala.

phosphatidylglycerols of general formula

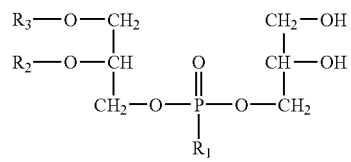

wherein $R_1$, $R_2$, and $R_3$ are defined above. Suitable phosphatidylglycerols suitable for use in the compositions and methods of the invention include, but are not limited to, the 1-acyl-2-acyl-sn-glycero-3-[phospho-rac-(1-glycerol)]s and the 1,2-diacyl-sn-glycero-3-[phospho-rac-(1-glycerol)]s, commercially available from Avanti Polar Lipids Inc. of Alabaster, Ala.

phosphatidylinositols of general formula

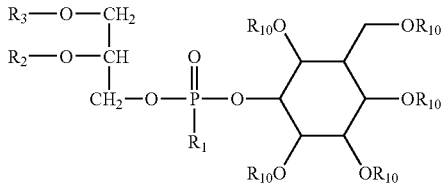

wherein $R_1$, $R_2$, $R_3$, and $R_{10}$ are defined above. Suitable phosphatidylinositols suitable for use in the compositions and methods of the invention include, but are not limited to, phosphatidylinositol, phosphatidylinositol-4-phosphate, and phosphatidylinositol-4,5-bisphosphate, commercially available from Avanti Polar Lipids Inc. of Alabaster, Ala.

The phospholipids are commercially available or can be obtained by methods well known to those skilled in the art. Representative methods for obtaining phospholipids are described in Sandra Pesch et al., *Properties of Unusual Phospholipids Bearing Acetylenic Fatty Acids, Tettrahedron*, vol. 15, no. 43, 14,627-14634 (1997); Sepp D. Kohlwein, *Phospholipid Synthesis, Sorting, Subcellular Traffic—The Yeast Approach*, Trends in Cell Biology, vol. 6, 260-266 (1996), Serguei V. Vinogradov, *Synthesis of Phospholipids—Oligodeoxyribonucleotide Conjugates*, Tett. Lett., vol. 36, no. 14, 2493-2496 (1995), and references cited therein.

In one embodiment, the phospholipid is Phospholipon®-80 (commercially available from Phospholipid GmbH of Cologne, Germany or American Lecithin Company of Oxford, Conn.).

In one embodiment, the phospholipid is Phospholipon®-80G (commercially available from Phospholipid GmbH of Cologne, Germany or American Lecithin Company of Oxford, Conn.).

In one embodiment, the phospholipid is Phospholipon®-85G (commercially available from Phospholipid GmbH of Cologne, Germany or American Lecithin Company of Oxford, Conn.).

In one embodiment, the phospholipid is Phospholipon®-1 00H (commercially available from Phospholipid GmbH of Cologne, Germany or American Lecithin Company of Oxford, Conn.).

The Sphingomyelin

Any pharmaceutically acceptable sphingomyelin can be used in the pharmaceutical compositions of the invention. In one embodiment, the sphingomyelin is

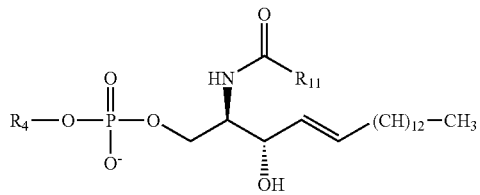

wherein $R_{11}$ is a $C_1$-$C_{24}$ linear, saturated or unsaturated hydrocarbon and $R_4$ is —$CH_2CH_2N(CH_3)_3^+$. In another embodiment, $R_{11}$ is a $C_8$-$C_{24}$ linear, saturated or unsaturated hydrocarbon and $R_4$ is —$CH_2CH_2N(CH_3)_3^+$. In another embodiment, $R_{11}$ is a $C_{16}$-$C_{24}$ linear, saturated or unsaturated hydrocarbon and $R_4$ is —$CH_2CH_2N(CH_3)_3^+$.

Suitable sphingomyelins include, but are not limited to, C2-Sphingomyelin, C6-Sphingomyelin, C18-Sphingomyelin, C6-NBD-Sphingomyelin, and C12-NBD Sphingomyelin, commercially available from Avanti Polar Lipids Inc. of Alabaster, Ala.

Similarly, in another embodiment, the amino acid-vitamin ester is an ester of lysine and the pharmaceutical composition further comprises a phosphatidyl choline. Without wishing to be bound by theory, it is believed that protonated phosphate groups on the phosphatidyl choline protonates the ε-amine group of lysine to provide a structure as depicted below:

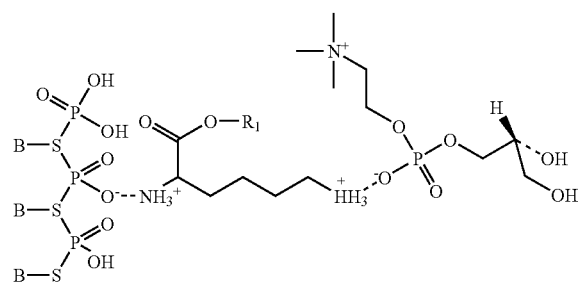

wherein S, B, and $R_1$ are defined above.

Without wishing to be bound by theory it is also believed that pharmaceutical compositions that comprise an amino acid-vitamin ester of lysine and further comprise a phospholipid, phosphatidyl choline, or a sphingomyelin that the amino acid-vitamin ester of lysine also forms structures wherein each amino group of the lysine ester or amide is protonated by a phospholipid, phosphatidyl choline, or sphingomyelin molecule. Such a structure is depicted below for a phospholipid:

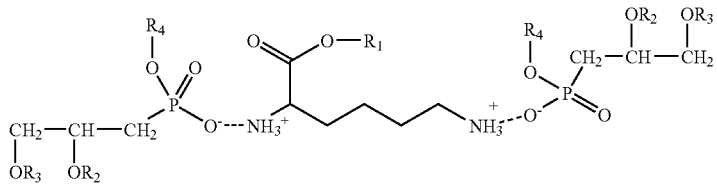

wherein $R_1$, $R_2$, $R_3$, and $R_4$ are defined above.

6.7.3.ii Pharmaceutical Compositions Comprising an Amino Acid-vitamin Ester of Aspartic Acid or Glutamic Acid and a Protonated Oligonucleotide In another embodiment, the amino acid-vitamin ester is an ester of aspartic acid or glutamic acid and the side chain carboxylic acid group of the aspartic acid or glutamic acid is also esterified, i.e., a diester of aspartic acid or glutamic acid. Without wishing to be bound by theory it is believed that the acidic phosphate groups of the oligonucleotide protonate the amine group of the diester of aspartic acid or glutamic acid to form a salt between diester of aspartic acid or glutamic acid and the aptamer as illustrated below for a diester of aspartic acid that is protonated by an oligonucleotide to provide a structure as depicted below:

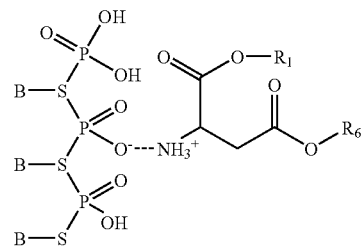

wherein S, B, and $R_1$ are defined above and $R_6$ is defined below.

The diesters of aspartic acid and glutamic acid have the structures:

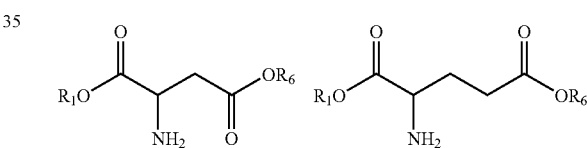

respectively, wherein $R_1$ is defined above and $R_6$ is the same as $R_1$. $R_1$ and $R_6$ can be the same or different. For example, each of $R_1$ and $R_6$ can be the residue of a vitamin and the residue of the vitamin can be the same or different. In another example, $R_1$ is the residue of a vitamin and $R_6$ is, for example a $C_1$-$C_{22}$ hydrocarbon group. Typically, however, $R_1$ and $R_6$ are the same.

The molar ratio of acidic groups on the oligonucleotide to the diester of aspartic acid or glutamic acid typically ranges from about 2:1 to 1:2. In one embodiment, the molar ratio of acidic groups on the oligonucleotide to the diester of aspartic acid or glutamic acid ranges from about 1.5:1 to 1:1.5. In one embodiment, the molar ratio of acidic groups on the oligonucleotide to the diester of aspartic acid or glutamic acid ranges from about 1.25:1 to 1:1.25. In one embodiment, the molar ratio of acidic groups on the oligonucleotide to the diester of aspartic acid or glutamic acid ranges from about 1.1:1. to 1:1.1. In one embodiment, the molar ratio of acidic groups on the oligonucleotide to the diester of aspartic acid or glutamic acid is about 1:1. A wider range for molar ratio of acidic groups on the oligonucleotide to the diester of aspartic acid or glutamic acid, however, is also possible. For example, the molar ratio of acidic groups on the oligonucleotide to the diester of aspartic acid or glutamic acid can range from about 15:1 to 1:15.

6.7.4 General Characteristics of the Pharmaceutical Compositions

Typically, when the compositions of the invention further comprising a pharmaceutically acceptable solvent are injected into water the resulting precipitate is a gummy mass or a gel. Typically, the viscosity of the gummy mass or a gel ranges from about 10,000 cP to 150,000 cP. In one embodiment, the viscosity of the gummy mass or a gel ranges from about 50,000 cP to 150,000 cP. In one embodiment, the viscosity of the gummy mass or a gel ranges from about 65,000 centipoise (cP) to 150,000 cP. In one embodiment, the viscosity of the gummy mass or a gel ranges from about 75,000 centipoise (cP) to 150,000 cP. The viscosity of the gummy mass or gel can be determined by injecting the pharmaceutical composition into water to provide the gummy mass or gel, removing the water and pharmaceutically acceptable organic solvent by filtering through a 0.22 µm filter to collect the gummy mass or gel, and then measuring the viscosity of the gummy mass or gel. Viscosity can be measured, for example, using a Brookfield DV-E Viscometer (commercially available from Brookfield of Middleboro, Mass.). In another embodiment, the precipitate is a solid, i.e., resistant to flow. In another embodiment, the solid is a crystalline solid.

The amino acid-vitamin ester used in the pharmaceutical composition can affect the rate of release of the pharmaceutically active compound or oligonucleotide from the drug depot. By varying the lipophilicity and/or molecular weight of the amino acid-vitamin ester it is possible to vary the rate at which the pharmaceutically active compound or oligonucleotide is released from the drug depot. Generally, the more lipophilic the amino acid-vitamin ester, the more slowly the pharmaceutically active compound or oligonucleotide is released. The lipophilicity and/or molecular weight of the amino acid-vitamin ester can be varied by varying the amino acid used to form the amino acid-vitamin ester. For example, the lipophilicity and/or molecular weight of the amino acid-vitamin ester can be varied by varying the R group of the amino acid or by varying the vitamin. For example, when R is a hydrocarbon group, the higher the molecular weight of R, the more lipophilic is the amino acid-vitamin ester.

The carboxylic acid used in the pharmaceutical composition can also affect the rate of release of the pharmaceutically active compound from the drug depot. Similarly, when the carboxylic acid is an N-acyl amino acid, the rate of release of the pharmaceutically active compound from the drug depot can be controlled by varying the lipophilicity and/or molecular weight of the N-acyl amino acid. Again, if the carboxylic acid or N-acyl amino acid is more lipophilic the drug is released more slowly. The lipophilicity and/or molecular weight of the carboxylic acid can be varied by varying the number of carbon atoms in the carboxylic acid. The lipophilicity and/or molecular weight of the N-acyl amino acid can be varied by varying the hydrocarbon group, $R_5$, of the acyl group, $R_2$, i.e., by varying the acyl group of formula —C(O)—$R_5$.

The pharmaceutical compositions may further include one or more additional excipients or additives well known to those of ordinary skill in the art. For example, the pharmaceutical formulations may include a preservative to inhibit microbial growth. Suitable preservatives include, but are not limited to, parabens such as methyl, ethyl, and propyl parabens; chlorobutanol; sodium benzoate; myristyl-gamma-picolinium chloride; benzyl alcohol; and ethyl alcohol. Preservatives, when present, are typically present in an amount of about 5 mg to 250 mg per mL of pharmaceutical composition and preferably about 5 mg to 100 mg per mL of pharmaceutical composition.

In one embodiment, the compositions include a local anesthetic such as lidocaine to lessen pain at the site of the injection.

Solid pharmaceutical compositions may further comprise additional excipients well known to those of ordinary skill in the art, such as binders, diluents, lubricants. Examples off suitable excipients are described in *Remington's Pharmaceutical Sciences* (Alfonso Gennaro ed., 19th ed. 1995), incorporated herein by reference. Accordingly, the solid pharmaceutical compositions can be formulated as a tablet, for oral administration, using methods will known to those skilled in the art (*Remington's Pharmaceutical Sciences* (Alfonso Gennaro ed., 19th ed. 1995).

Similarly, the pharmaceutical compositions in the form of a gel can be formulated for oral administration by encapsulating the pharmaceutical composition in a capsule, such as a hard or soft gelatin capsule.

The components of the pharmaceutical composition (the amino acid-vitamin ester, the carboxylic acid, the organic solvent, the pharmaceutically active compound, and the oligonucleotide, as well as any other optional components) are preferably biocompatible and non-toxic and, over time, are simply absorbed and/or metabolized by the body.

6.8 Manufacturing the Pharmaceutical Compositions

To prepare the pharmaceutical compositions of the invention comprising (i) an amino acid-vitamin ester, (ii) an acidic pharmaceutically active compound, and (iii) a pharmaceutically acceptable organic solvent, the amino acid-vitamin ester and the acidic pharmaceutically active compound are simply dissolved in the pharmaceutically acceptable organic solvent to provide a solution (typically about 90% of the amount of the solvent desired in the final pharmaceutical composition). Additional excipients and/or additives can then be dissolved in the solution. Additional pharmaceutically acceptable organic solvent is then added to provide the desired concentration of the amino acid-vitamin ester and the acidic pharmaceutically active compound in the pharmaceutical composition. The solution of the amino acid-vitamin ester and the acidic pharmaceutically active compound, and additional excipients and/or additives can then be filtered, preferably sterile filtered, directly into bottles.

The solid pharmaceutical compositions comprising a (i) an amino acid-vitamin ester and (ii) an acidic pharmaceutically active compound are prepared in the same way as is used to prepare the pharmaceutical compositions of the invention comprising (i) an amino acid-vitamin ester, (ii) an acidic pharmaceutically active compound, and (iii) a pharmaceutically acceptable organic solvent, and the pharmaceutically acceptable organic solvent is simply removed by evaporation. In one embodiment, the pharmaceutically acceptable organic solvent is removed under reduced pressure. Alternatively, the pharmaceutical composition comprising (i) an amino acid-vitamin ester, (ii) an acidic pharmaceutically active compound, and (iii) a pharmaceutically acceptable organic solvent can be diluted with water to provide a solid precipitate and the solid precipitate collected by filtration and, optionally, dried. The resulting solid pharmaceutical composition can optionally be milled to provide smaller particles. Excipients can also be added to the resulting solid pharmaceutical compositions.

Similarly, to prepare the pharmaceutical compositions of the invention comprising (i) an amino acid-vitamin ester, (ii) a carboxylic acid, (iii) a neutral non-acidic pharmaceutically active compound or a pharmaceutically acceptable salt of a pharmaceutically active compound, and (iv) a pharmaceutically acceptable organic solvent, the amino acid-vitamin ester, the carboxylic acid, and the neutral non-acidic pharmaceutically active compound or a pharmaceutically acceptable salt of a pharmaceutically active compound are simply dissolved in the pharmaceutically acceptable organic solvent to provide a solution (typically about 90% of the amount of the solvent desired in the final pharmaceutical composition). Additional excipients and/or additives can then be dissolved in the solution. Additional pharmaceutically acceptable organic solvent is then added to provide the desired concentration of the amino acid-vitamin ester, the carboxylic acid, and the neutral non-acidic pharmaceutically active compound or pharmaceutically acceptable salt of a pharmaceutically active compound in the pharmaceutical composition. The solution of the amino acid-vitamin ester, the carboxylic acid, the neutral non-acidic pharmaceutically active compound or pharmaceutically acceptable salt of a pharmaceutically active compound, and additional excipients and/or additives can then be filtered, preferably sterile filtered, directly into bottles.

The solid pharmaceutical compositions comprising a (i) an amino acid-vitamin ester, (ii) a carboxylic acid, and a (iii) a neutral non-acidic pharmaceutically active compound or a pharmaceutically acceptable salt of a pharmaceutically active compound are prepared in the same way as is used to prepare the pharmaceutical compositions of the invention comprising (i) an amino acid-vitamin ester, (ii) a carboxylic acid, and a (iii) a neutral non-acidic pharmaceutically active compound or a pharmaceutically acceptable salt of a pharmaceutically active compound and (iv) a pharmaceutically acceptable organic solvent, and the pharmaceutically acceptable organic solvent is simply removed by evaporation. In one embodiment, the pharmaceutically acceptable organic solvent is removed under reduced pressure. Alternatively, the pharmaceutical composition comprising (i) an amino acid-vitamin ester, (ii) a carboxylic acid, a (iii) a neutral non-acidic pharmaceutically active compound or a pharmaceutically acceptable salt of a pharmaceutically active compound, and a pharmaceutically acceptable organic solvent can be diluted with water to provide a solid precipitate and the solid precipitate collected by filtration and, optionally, dried. The resulting solid pharmaceutical composition can optionally be milled to provide smaller particles. Excipients can also be added to the resulting solid pharmaceutical compositions.

The pharmaceutical compositions comprising an amino acid-vitamin ester and a protonated oligonucleotide can be prepared by the following method. The inorganic salt of the oligonucleotide, typically a potassium or sodium salt, is dissolved in a solvent in which it is soluble, for example methanol or water, and the pH of the resulting solution is adjusted to a value of between about 2 and 3 with an organic acid, such as formic acid, as depicted below:

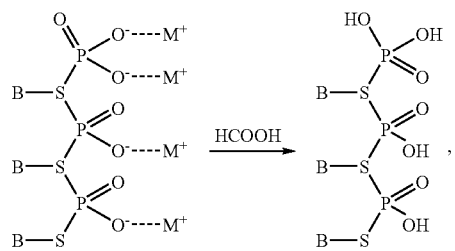

wherein S and B are defined above and M$^+$ is a metal ion, to provide a solution of the protonated oligonucleotide.

The resulting solution of protonated oligonucleotide is then dialyzed against water to remove excess formic acid and formate salts and if, for example, the neutralization is conducted in a methanol solvent, to replace the methanol with water. The water can then be removed from the aqueous solution of the protonated oligonucleotide by lyophilization to provide the protonated oligonucleotide or, alternatively, the aqueous solution of the protonated oligonucleotide can be dialyzed against methanol to replace the water with methanol and then simply removing the methanol under reduced pressure to provide the protonated oligonucleotide.

A solution of the protonated oligonucleotide can also be prepared using a cation exchange resin. Any cation exchange resin known to one skilled in the art can be used, for example, a Strata®SCX cation exchange resin (commercially available from Phenomenex of Torrance, Calif.) or a DOWEX® cation exchange resin, such as DOWEX®50 (commercially available from Dow Chemical Company of Midland, Mich.) can be used. Typically, a column containing the cation exchange resin is first washed with an acidic solution to protonate the resin and then a solution of the inorganic salt of the oligonucleotide, typically a potassium or sodium salt, in a solvent, for example methanol or water, is passed through the resin to provide, as the eluant, a solution of the protonated oligonucleotide.

To prepare the pharmaceutical compositions comprising a protonated oligonucleotide and an amino acid-vitamin ester, the protonated oligonucleotide is dissolved in a solvent, such as methanol, typically with stirring, and to the resulting solution is then added the amino acid-vitamin ester, as depicted below:

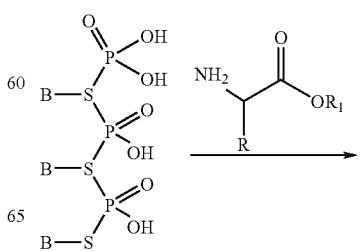

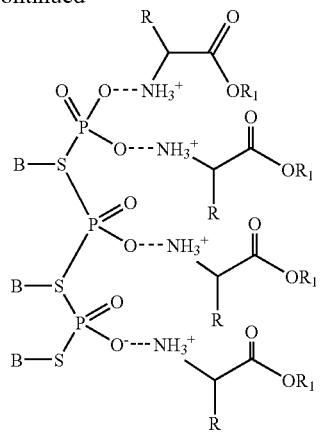

wherein S, B, R, and $R_1$ are defined above.

Any other components of the pharmaceutical composition, such as a carboxylic acid, phospholipid, phosphatidyl choline, or sphingomyelin are then added to the resulting solution.

Typically, sufficient amino acid-vitamin ester, and any other components, are added to provide a solution having a pH value ranging from about 5 to 9. In one embodiment, sufficient amino acid-vitamin ester, and any other components, are added to provide a solution having a pH value ranging from about 6 to 8. In one embodiment, sufficient amino acid-vitamin ester, and any other components, are added to provide a solution having a pH value of about 7. The pH can be readily measured by removing a few microliters of the solution and applying it to a wet pH test strip (such as commercially available from Sigma-Aldrich of Milwaukee, Wis.) that indicates the pH of the solution by the color of the test strip after the solution is applied. The solvent is then removed under reduced pressure to provide the pharmaceutical composition comprising the amino acid-vitamin ester and the oligonucleotide. The resulting composition can then be dissolved in a pharmaceutically acceptable organic solvent to provide the pharmaceutical composition comprising the amino acid-vitamin ester, the protonated oligonucleotide, and a pharmaceutically acceptable organic solvent. Alternatively, the pharmaceutical compositions comprising a protonated oligonucleotide, an amino acid-vitamin ester, and any other components, and a pharmaceutically acceptable organic solvent can be prepared by dissolving the protonated oligonucleotide in the pharmaceutically acceptable organic solvent and adding the amino acid-vitamin ester and any other components to the resulting solution, preferably with stirring, to provide the pharmaceutical composition.

The pharmaceutical compositions can be sterilized using an autoclave.

The invention further relates to a method of manufacturing the pharmaceutical composition of the invention.

6.9 Methods of Treating a Condition in an Animal

The invention further relates to a method of treating or preventing a condition in an animal. The method comprises administering to an animal in need thereof an effective amount of a pharmaceutical composition of the invention.

In one embodiment, the invention relates to methods of treating a condition in an animal comprising administering to an animal in need thereof an effective amount of a pharmaceutical composition of the invention.

In one embodiment, the invention relates to methods of preventing a condition in an animal comprising administering to an animal in need thereof an effective amount of a pharmaceutical composition of the invention.

Methods of administration include, but are not limited to, intradermal, intramuscular, intraperitoneal, intravenous, subcutaneous, intranasal, epidural, oral, sublingual, intracerebral, intravaginal, transdermal, rectal, by inhalation, or topical. The mode of administration is left to the discretion of the practitioner. In most instances, administration will result in the release of the pharmaceutically active compound or oligonucleotide into the bloodstream.

In one embodiment, the pharmaceutical composition of the invention is administered by injection. In one embodiment, the pharmaceutical composition of the invention is administered orally. In one embodiment, the pharmaceutical composition of the invention is administered topically.

In one embodiment, the method of treating or preventing a condition in an animal comprises administering to the animal in need thereof an effective amount of a pharmaceutical composition of the invention by parenterally administering the pharmaceutical composition of the invention. In one embodiment, the pharmaceutical composition is administered by infusion or bolus injection. In one embodiment, the pharmaceutical composition is administered subcutaneously.

In one embodiment, the method of treating or preventing a condition in an animal comprises administering to the animal in need thereof an effective amount of a pharmaceutical composition of the invention by orally administering the pharmaceutical composition of the invention. In one embodiment, the composition is in the form of a capsule or tablet.

The pharmaceutical compositions can also be administered by any other convenient route, for example, topically, by absorption through epithelial or mucocutaneous linings (e.g., oral, rectal, and intestinal mucosa, etc.).

Solid pharmaceutical compositions can be administered by implanting the solid pharmaceutical composition under the skin of the animal. Solid pharmaceutical compositions, however, may also be administered by injecting an animal with a suspension of the solid pharmaceutical composition in a pharmaceutically acceptable organic solvent.

The pharmaceutical compositions of the invention in the form of a solid, a crystal, a gummy mass or a gel can also be administered orally. For example, encapsulating the pharmaceutical formulations in the form of a solid, a crystal, a gummy mass or a gel in a capsule provides a dosage form that can be administered orally. Furthermore, solid pharmaceutical compositions of the invention can be combined with an excipient such as a binder, diluent, or lubricant and formulated into a tablet to provide a dosage form for oral administration. See, for example, *Remington's Pharmaceutical Sciences*, Alfonso Gennaro ed., 19th ed. 1995), incorporated herein by reference. Oral dosage forms can be designed to release the pharmaceutically active compound in the stomach immediately or almost immediately or to provide sustained release of the pharmaceutically active compound in the stomach. The rate of release of the pharmaceutically active compound is varied by varying the lipophilicity and/or molecular weight of the components of the pharmaceutical composition.

Injectable pharmaceutical compositions are administered to an animal by injecting the animal with the pharmaceutical composition. When the injectable pharmaceutical compositions are injected into an animal, the pharmaceutical compositions typically form a depot that provides sustained-release of the pharmaceutically active compound. Pharmaceutical compositions that are a suspension of the solid pharmaceutical composition in a pharmaceutically acceptable organic solvent can also form a depot that provides sustained-release of the pharmaceutically active compound when injected into an animal. The components of the pharmaceutical composition, i.e., the amino acid-vitamin ester, the carboxylic acid, and the pharmaceutically acceptable organic solvent are biocompatible and non-toxic and, over time, are simply absorbed and/or metabolized by the body. For example, the amino acid-vitamin ester is simply hydrolyzed to provide an amino acid and a vitamin, each of which are non-toxic and, in fact, can be utilized by the animal.

The pharmaceutical compositions can be administered systemically or locally.

The pharmaceutical compositions can be administered together with another biologically active agent.

The pharmaceutical compositions of the invention can provide an effective amount of the pharmaceutically active compound or pharmaceutically acceptable salt thereof or the oligonucleotide to the animal for a period of up to 15 days, and even longer, depending on components of the pharmaceutical composition, i.e., the pharmaceutically active compound or pharmaceutically acceptable salt thereof, the oligonucleotide, the amino acid-vitamin ester, the carboxylic acid, and the pharmaceutically acceptable organic solvent.

In one embodiment, the pharmaceutical composition provides an effective amount of the pharmaceutically active compound or a pharmaceutically acceptable salt thereof or the oligonucleotide for up to about 3 days.

In one embodiment, the pharmaceutical composition provides an effective amount of the pharmaceutically active compound or a pharmaceutically acceptable salt thereof or the oligonucleotide for up to about 4 days.

In one embodiment, the pharmaceutical composition provides an effective amount of the pharmaceutically active compound or a pharmaceutically acceptable salt thereof or the oligonucleotide for up to about 6 days.

In one embodiment, the pharmaceutical composition provides an effective amount of the pharmaceutically active compound or a pharmaceutically acceptable salt thereof or the oligonucleotide for up to about 8 days.

In one embodiment, the pharmaceutical composition provides an effective amount of the pharmaceutically active compound or a pharmaceutically acceptable salt thereof or the oligonucleotide for up to about 10 days.

In one embodiment, the pharmaceutical composition provides an effective amount of the pharmaceutically active compound or a pharmaceutically acceptable salt thereof or the oligonucleotide for up to about 12 days.

In one embodiment, the pharmaceutical composition provides an effective amount of the pharmaceutically active compound or a pharmaceutically acceptable salt thereof or the oligonucleotide for up to about 15 days.

The pharmaceutical compositions are useful in human medicine and veterinary medicine. The pharmaceutical compositions are particularly useful in veterinary medicine.

In one embodiment, the animal is a human.
In one embodiment, the animal is a cat.
In one embodiment, the animal is a dog.
In one embodiment, the animal is a cow.
In one embodiment, the animal is a pig.
In one embodiment, the animal is a sheep.
In one embodiment, the animal is a horse.

Typically, the pharmaceutical composition further comprising a pharmaceutically acceptable organic solvent is injected in an amount of between about 0.2 mL and 15 mL, preferably between about 0.5 mL and 12 mL, more preferably between about 1 mL and 10 mL. The precise dose to be administered will depend on the seriousness of the condition, and the animal being treated and can be decided according to the judgment of a practitioner and/or each animal's circumstances. Smaller animals typically receive smaller injection volumes. For example, the injection volume for a cat is typically about 1 mL and the injection volume for a dog is typically between about 1 mL and 2 mL. For large animals such as cows and horses, however, the injection volume can be as large as 10 mL and even larger. The amount of the pharmaceutical composition administered to an animal can be determined by standard clinical techniques. In addition, in vitro or in vivo assays can optionally be employed to help identify optimal dosage ranges.

The pharmaceutical composition further comprising a pharmaceutically acceptable organic solvent can be administered, for example, by an intramuscular, intraperitoneal, or subcutaneous injection.

Solid pharmaceutical compositions are typically administered by implanting the solid pharmaceutical compositions containing between about 0.01 and 2 g, preferably between about 0.2 g and 1.5 g, of the pharmaceutically active compound or pharmaceutically acceptable salt thereof or the oligonucleotide under the skin of the animal using methods well known to one of ordinary skill in the art. Solid pharmaceutical compositions can also be administered by injecting a suspension or solution of the solid composition in a solvent. The solid pharmaceutical composition can be suspended in an aqueous solvent or an organic solvent.

Pharmaceutical compositions for oral administered are typically in the form of a capsule or tablet and typically contain between about 0.001 g and 2 g, preferably between about 0.01 g and 1.5 g, the pharmaceutically active compound or pharmaceutically acceptable salt thereof or the oligonucleotide.

Advantageously, the pharmaceutical compositions, by providing sustained release of the pharmaceutically active compound, have reduced toxicity, particularly in small animal such as cats and dogs. Accordingly, the pharmaceutical compositions of the invention have a better therapeutic profile that conventional immediate release formulations. The methods of the invention, which involve administering a pharmaceutically active compound or oligonucleotide to an animal by injecting the animal with a pharmaceutical composition of the invention, permit pharmaceutically active compounds and oligonucleotide to be administered to animals that could, if administered in presently available dosage forms, result in toxicity and even death of the animal being treated. By providing sustained release of the pharmaceutically active compound or the oligonucleotide, the pharmaceutical compositions of the invention need to be administered less frequently and therefore are also easier to administer, more convenient, and more cost effective than conventional modes of administering pharmaceutically active compounds and oligonucleotides. Another beneficial feature of the pharmaceutical compositions of the invention is that the amino acid-vitamin ester component is simply hydrolyzed in the animals body to provide an amino acid and a vitamin, each of which are non-toxic and, in fact, can be advantageously utilized by the animal.

6.10 Kits

The invention encompasses kits that can simplify the administration of a pharmaceutically active compound or oligonucleotide to an animal. A typical kit of the invention comprises a unit dosage form of a pharmaceutical composition of the invention. In one embodiment, the unit dosage form is a container, such as a vial, which can be sterile, containing a pharmaceutical composition of the invention. The kit can further comprise a label or printed instructions instructing the use of the pharmaceutically active compound to treat a condition. In another embodiment, the kit comprises a unit dosage form of a pharmaceutical composition of the invention and a syringe for administering the pharmaceutical composition.

The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

7. EXAMPLES

Example 7.1

Measuring in Vitro Release of the Pharmaceutically Active Compound from the Composition In vitro release of the pharmaceutically active compound from the compositions of the invention can be determined by the following method. An aliquot (about 1 mL) of the pharmaceutical compositions is sealed in a dialysis bag (commercially available from Pierce Biotechnology, Inc. of Rockford Ill.) and the dialysis bag suspended in a flask containing about 150 mL of phosphate buffered saline at pH 7.4. Aliquots of saline are then removed at various intervals and the concentration of the pharmaceutically active compound determined using any analytical method known to those skilled in the art.

For example, when the pharmaceutically active compound is flunixin, high pressure liquid chromatography (HPLC) can be used as the analytical method. The following HPLC analysis can be used when the pharmaceutically active compound is flunixin:

About 100 μL of the saline solution is injected on a Phenomenex LUNA 5 μM phenyl-hexyl 100 Å, 250×4.6 mm analytical column operated at a flow rate of 1.7 mL/min. The HPLC is interfaced to a UV detector operated at 285 nm. The HPLC column is eluted using gradient elution according to the following profile:

| Time | Percent Pump A | Percent Pump B |
|------|----------------|----------------|
| 0    | 30             | 70             |
| 10.5 | 85             | 15             | wherein the solvent in pump A is 25 mM phosphate buffer at pH 2.4 and the solvent in pump B is acetonitrile. The total run time is 25 min. The concentration of flunixin is then determined by comparing the area under the curve for the HPLC peak corresponding to flunixin to a standard curve of peak areas v. known concentrations of flunixin in phosphate-buffered saline. The standard curve can be prepared using the following concentrations of flunixin 4, 2, 1, 0.5, and 0 g/mL.

Example 7.2

Preparation of N-acyl Amino Acids

Phenylalanine butyramide: 5 g of phenylalanine was added to 20 mL of butyric anhydride and the resulting mixture heated to about 100° C. for about 3 h. Excess butyric anhydride was then removed under reduced pressure to provide a solid residue that was recrystallized from ethanol to provide phenylalanine butyramide.

Example 7.3

Synthesis of Vitamin Amino Acid Esters

Esters of naturally occurring vitamin and amino acid are synthesized as follows. A boc-protected amino acid (30.7 mmol) is dissolved in anhydrous tetrahydrofuran (200 mL) under an argon atmosphere, the mixture cooled to 4° C. in an ice bath, and activated by adding carbonyldiimidazole (5 g, 30.1 mmol). The resulting reaction mixture is then warmed to room temperature and allowed to further react for 1 hour. A vitamin containing a hydroxyl group (for example, vitamin E or vitamin A) is then added to the mixture and the mixture heated to 50° Celsius. After 24 hours the reaction mixture is cooled to room temperature and the tetrahydrofuran removed under reduced pressure. The resulting oil is dissolved in ethyl acetate and extracted twice with 0.25M HCl and the organic layer is dried using sodium sulfate and evaporated to dryness. Further purification is achieved using column chromatography with a silica gel solid support and eluting with 20% methyl tert-butyl ether/hexane. The resulting yield is approximately 16.3 mmol of boc protected amino acid vitamin ester (m/z 761.0, when the vitamin is α-tocopherol and the amino acid is lysine).

Purified vitamin-amino acid ester salts with trifluoroacetic acid are obtained by stirring the vitamin-amino acid ester in 30% trifluoroacetic/dichloromethane (50 mL) for 2 hours. Dichloromethane and excess trifluoroacetic acid are then removed under reduced pressure and the salt dissolved in fresh dichloromethane (200 mL). DOWEX anion exchange resin (sigma Aldrich St. Louis Miss.) (200 mL, 200 mmol pyridinium ion) is then added and the resulting mixture stirred for 30 minutes and filtered to provide the free base of the vitamin-amino acid ester. Further purification is achieved by loading the free base onto a tosic acid functionalized silica gel (commercially available from Siliscycle, Inc. of Quebec, Canada), (27.5 g, 1.2 eq), washing with dichloromethane, and eluting with equivalents of triethlyamine in dichloromethane. Removal of solvent under vacuum resulted in an orange to yellow colored oil (m/z 560.6, when the vitamin is α-tocopherol and the amino acid is lysine).

Example 7.4

Formulation of Flunixin with α-Tocopherol Lysine Ester 500 mg of flunixin was weighed into a 5 mL volumetric flask. 500 μL of propylene glycol followed by approximately 3.5 mL of stabilized glycerol formal was then added to the volumetric flask. α-Tocopherol lysine ester (1.04 g., about 1.1 equivalents) was added to the volumetric flask and the resulting mixture was mixed with occasional sonication to provide clear homogeneous solution. The clear orange solution was made to a final volume of 5 mL and mixed thoroughly to provide the final formulation.

The structure of α-tocopherol lysine ester is

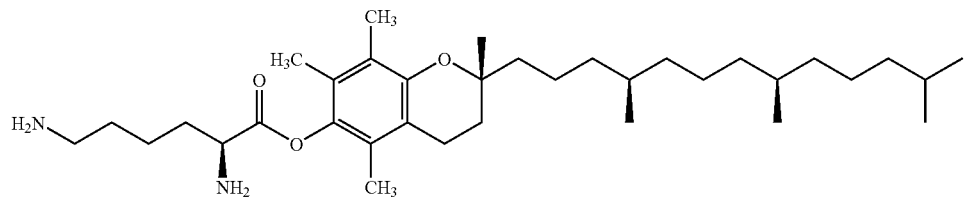 [SMILES: Cc1c(C)c2c(c(C)c1OC(=O)[C@@H](N)CCCCN)CC[C@@](C)(CCC[C@H](C)CCC[C@H](C)CCCC(C)C)O2]

The structure of flunixin is

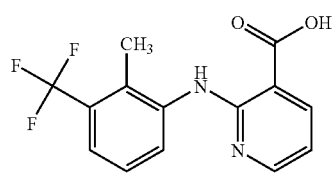 [SMILES: Cc1c(Nc2ncccc2C(=O)O)cccc1C(F)(F)F]

100 μL of the resulting formulation was injected into 3 mL of deionized water contained in a clear vial using a 1 mL syringe equipped with a 22 gauge needle. A string like precipitate was observed to form initially as the solvent diffused away. After mixing a white solid was deposited on the sides and the bottom of the vial. With less vigorous mixing, a lump or concentrated solid was observed to form.

Example 7.5

Formulation of Carprofen with α-Tocopherol Lysine Ester 500 mg of carprofen was weighed into 5 mL volumetric flask. 500 μL of propylene glycol followed by approximately 3.5 mL of stabilized glycerol formal was then added to the volumetric flask. α-Tocopherol Lysine ester (1.13 g, about 1.1 equivalents) was then added to the volumetric flask and the resulting mixture was mixed with occasional sonication to provide clear homogeneous solution. The clear orange solution was made to a final volume of 5 mL and mixed thoroughly to provide the final formulation.

The structure of carprofen is

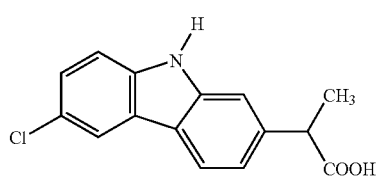 [SMILES: CC(C(=O)O)c1ccc2c(c1)[nH]c1ccc(Cl)cc12]

100 μL of the resulting formulation was injected into 3 mL of deionized water contained in a in clear vial using a 1 mL syringe equipped with a 22 gauge needle. A string like precipitate was observed to form initially as the solvent diffused away. After mixing a white solid was deposited on the sides and the bottom of the vial. With less vigorous mixing, a lump or concentrated solid was observed to form.

Example 7.6

Formulation of an Oligonucleotide with α-Tocopherol Phenylalanine Ester

α-Tocopherol phenylalanine ester (28.29 mg, 6 eq) was dissolved in 100 μL of dimethylacetamide. To the resulting solution was added 16.5 mg (1 eq) of a 23 nucleotide protonated aptamer followed by an additional 100 μL of dimethylacetamide. The resulting mixture was then warmed to 37° C. to provide a clear solution. The aptamer was similar to ARC259, described above, except that the aptamer was pegylated at both the 3'-end and the 5'-end, rather than only at the 5'-end, with a PEG moiety having an average molecular weight of 20 kD.

To evaluate the ability of the resulting formulation to form a depot, 10 μL of the formulation was added to 1 mL of phosphate buffered saline (10 mm phosphate buffer, 120 mm saline, pH 7.4) followed by brief mixing. A clear, gelatinous, cloth-like continuous solid depot was observed to form. The resulting mixture was then centrifuged for 10 minutes at 13,000 times the force of gravity. The resulting clear supernatant was separated from the pellet and analyzed by fluorescence using Oligreen oligonucleotide quantitation reagent (commercially available from Invitrogen, Carlsbad, Calif.) following the assay methodology provided by Invitrogen. Less than 5% of the total oligonucleotide was contained in the supernatant, indicating that the oligonucleotide was entrapped in the depot.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosure of which are incorporated herein by reference.

What is claimed is:

1. A pharmaceutical composition comprising:
   (i) a protonated oligonucleotide,
   (ii) an amino acid-vitamin ester, and
   (iii) a pharmaceutically acceptable organic solvent,
wherein the pharmaceutical composition is injectable and forms a precipitate when injected into water.

2. The pharmaceutical composition of claim 1, wherein the amino acid-vitamin ester is an ester of an amino acid selected from the group consisting of glycine, alanine, valine, leucine, isoleucine, phenylalanine, asparagine, glutamine, tryptophane, proline, serine, threonine, tyrosine, hydroxyproline, cysteine, methionine, aspartic acid, glutamic acid, lysine, arginine, and histidine.

3. The pharmaceutical composition of claim 1, wherein the amino acid-vitamin ester is an ester of a vitamin selected from the group consisting of vitamin A, vitamin $B_1$, vitamin $B_2$, vitamin $B_5$, vitamin $B_6$, vitamin $B_{12}$, vitamin C, vitamin D, and vitamin E.

4. The pharmaceutical composition of claim 2, wherein the amino acid-vitamin ester is an ester of lysine.

5. The pharmaceutical composition of claim 4 further comprising a carboxylic acid.

6. The pharmaceutical composition of claim 5, wherein the carboxylic acid is a $C_1$-$C_{22}$ carboxylic acid.

7. The pharmaceutical composition of claim 5, wherein the carboxylic acid is a $C_1$-$C_6$ carboxylic acid.

8. The pharmaceutical composition of claim 5, wherein the carboxylic acid is a $C_6$-$C_{18}$ carboxylic acid.

9. The pharmaceutical composition of claim 5, wherein the carboxylic acid is selected from the group consisting of acetic acid, propionic acid, butanoic acid, pentanoic acid, hexanoic acid, benzoic acid, caproic acid, lauric acid, myristic acid, palmitic acid, stearic acid, palmic acid, oleic acid, linoleic acid, and linolenic acid.

10. The pharmaceutical composition of claim 5, wherein the carboxylic acid is a N-acyl amino acid of general formula:

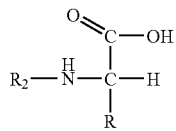

wherein
R is a straight chain or cyclic hydrocarbon group, an aromatic group, or an aromatic or non-aromatic heterocyclic group that can be optionally substituted; and
$R_2$ is an acyl group of formula —C(O)—$R_5$, wherein $R_5$ is a substituted $C_1$ to $C_{21}$ hydrocarbon group.

11. The pharmaceutical composition of claim 10, wherein $R_5$ is a $C_5$- to $C_{21}$ hydrocarbon group.

12. The pharmaceutical composition of claim 10, wherein $R_2$ is an acyl group selected from the group consisting of acetyl, propionyl, butanoyl, hexanoyl, caproyl, heptoyl, octoyl, nonoyl, decoyl, undecoyl, dodecoyl, tridecoyl, tetradecoyl, pentadecoyl, hexadecoyl, heptadecoyl, octadecoyl, laurolyl, myristoyl, palmitoyl, stearoyl, palmioleoyl, oleoyl, linoleoyl, linolenoyl, and benzoyl.

13. The pharmaceutical composition of claim 4, further comprising a phospholipid, a sphingomyelin, or phosphatidyl choline.

14. The pharmaceutical composition of claim 1, wherein the solvent is selected from the group consisting of pyrrolidone, N-methyl-2-pyrrolidone, polyethylene glycol, propylene glycol, glycerol formal, isosorbid dimethyl ether, ethanol, dimethyl sulfoxide, tetraglycol, tetrahydrofurfuryl alcohol, triacetin, propylene carbonate, dimethyl acetamide, dimethyl formamide, dimethyl sulfoxide, and combinations thereof.

15. The pharmaceutical composition of claim 1, wherein the oligonucleotide is selected from the group consisting of double stranded DNA, single stranded DNA, and RNA.

16. The pharmaceutical composition of claim 1, wherein the oligonucleotide is selected from the group consisting of an aptamer, an antisense nucleic acid, and SiRNA.

17. The pharmaceutical composition of claim 1, wherein combined amount of the oligonucleotide and amino acid-vitamin ester in the pharmaceutical compositions ranges from about 10 to 60 percent by weight of the pharmaceutical composition.

18. A method of treating a condition in an animal comprising administering to an animal in need thereof the pharmaceutical composition of claim 1.

19. The method of claim 18, wherein the administering is by injection.

* * * * *